(12) United States Patent
Pedersen et al.

(10) Patent No.: US 10,032,287 B2
(45) Date of Patent: Jul. 24, 2018

(54) SYSTEM AND METHOD FOR ASSESSING WOUND

(71) Applicants: Peder C. Pedersen, Sterling, MA (US); Diane M. Strong, Worcester, MA (US); Emmanuel Agu, Ashland, MA (US); Bengisu Tulu, Newton, MA (US); Lei Wang, Worcester, MA (US); Qian He, Worcester, MA (US)

(72) Inventors: Peder C. Pedersen, Sterling, MA (US); Diane M. Strong, Worcester, MA (US); Emmanuel Agu, Ashland, MA (US); Bengisu Tulu, Newton, MA (US); Lei Wang, Worcester, MA (US); Qian He, Worcester, MA (US)

(73) Assignee: Worcester Polytechnic Institute, Worcester, MA (US)

(*) Notice: Subject to any disclaimer, the term of this patent is extended or adjusted under 35 U.S.C. 154(b) by 165 days.

(21) Appl. No.: 14/528,397

(22) Filed: Oct. 30, 2014

(65) Prior Publication Data
US 2015/0119721 A1 Apr. 30, 2015

Related U.S. Application Data

(60) Provisional application No. 61/897,559, filed on Oct. 30, 2013, provisional application No. 61/898,907, filed on Nov. 1, 2013.

(51) Int. Cl.
G06T 7/00 (2017.01)
G06T 7/40 (2017.01)
A61B 5/00 (2006.01)
G06T 7/11 (2017.01)
(Continued)

(52) U.S. Cl.
CPC ............. *G06T 7/408* (2013.01); *A61B 5/445* (2013.01); *G06T 7/0012* (2013.01); *G06T 7/11* (2017.01); *G06T 7/194* (2017.01); *G06T 7/90* (2017.01); *G06T 2207/10024* (2013.01); *G06T 2207/20076* (2013.01); *G06T 2207/20081* (2013.01); *G06T 2207/30088* (2013.01)

(58) Field of Classification Search
None
See application file for complete search history.

(56) References Cited

U.S. PATENT DOCUMENTS 5,625,501 A * 4/1997 Taggert ................. A45D 42/18
  359/855
6,518,963 B1 2/2003 Waupotitsch et al.
2003/0085908 A1 5/2003 Luby
(Continued)

FOREIGN PATENT DOCUMENTS

WO 2013149038 A1 10/2013
WO WO 2013/149038 A1 * 10/2013 ............... G06K 9/78

OTHER PUBLICATIONS

Comaniciu et al. 2002 IEEE Trans. Pattern Analysis and Machine Intelligence 24:603-619; Pub.Dat. 2002.*
(Continued)

Primary Examiner — Tse Chen
Assistant Examiner — Patrick M Mehl
(74) Attorney, Agent, or Firm — Burns & Levinson LLP; Orlando Lopez

(57) ABSTRACT

The wound assessing method and system of the present teachings provide a convenient, quantitative mechanism for diabetic foot ulcer assessment.

8 Claims, 27 Drawing Sheets

(51) Int. Cl.
    *G06T 7/90*     (2017.01)
    *G06T 7/194*     (2017.01)

(56) References Cited

U.S. PATENT DOCUMENTS

| | | |
|---|---|---|
| 2004/0136579 A1 | 7/2004 | Gutenev |
| 2010/0091104 A1 | 4/2010 | Sprigle et al. |
| 2010/0113940 A1 | 5/2010 | Sen et al. |
| 2012/0259230 A1 | 10/2012 | Riley |

OTHER PUBLICATIONS

Houghton et al. 2000 Ostomy Wound Management 46:20-30; Pub. Date Apr. 2000.*
Bus et al 2010 J.Med.Engin.Technol. 34:43-50; Pub.Date online Dec. 1, 2009.*
Xiao et al. 2010 CIKM2010 1701-1704; Pub.Date Oct. 2010.*
Wannous et al. 2010 J. Electronic Imaging 19:023002-1-023002-9; Pub.Date online Apr. 2010.*
PictZar 2011 PictZar® CDM / Professional: Calibrated Digital Measurements; https://web-beta.archive.org/web/20131030232823/http://www.pictzar.com/PictZar.htm 5 pages; Pub.Date 2011.*
Wang et al 2016 J. Diab. Scie. Technol. 10: 421-428.*

International Search Report and Written Opinion dated Feb. 17, 2015 for PCT/US14/63108.
Fei-Fei, L. et al. A Bayesian Hierarchical Model for Learning Natural Scene Categories. IEEE Computer Society Conference on Computer Vision and Pattern Recognition (vol. 2), Jun. 2005: 524-531.
Banchev, B. 2014 at https://www.researchgate.net/publication/267750847 "Wound size measurement and 30 reconstruction using structured light, ground work and analysis of requirements." 8 pages.
Gallagher, B.A. "Wound Bed Assessment Using Calibrated Images and Representation in OpenEHR." 2012 MS thesis in Health Informatics, University of Dublin, 208 pages.
He, X. et al. "Multiscale Conditional Random Fields for Image ." IEEE Comp. Sac. Conf. on Computer Vision and Pattern Recognition CVPR'04, 8 pages.
Morgan, N. 2015 "Wound Assessment: the Basic's." Wound Care Education Institute, at www.kci- medical.com, 100 pages.
Veredas, F. et al. "Binary Tissue Classification on Wound Images With Neural Networks and Bayesian Classifiers," 2010 IEEE Trans. Med. Image 29:410-427.
Wang, L. et al. "Wound Image Analysis System for Diabetics," 2013 Proc.SPIE 8669:866924-1-866924-14.
Wang, L. et al. "Smartphone-Based Wound Assessment System for Patients With Diabetes," 2014 IEEE Trans. BioMed.Engin. 62:477-488.

* cited by examiner

```
                        actual class
                        (observation)

tp              fp
                 (true positive)  (false positive)
predicted class  Correct result   Unexpected result
 (expectation)       fn              tn
                 (false negative) (true negative)
                 Missing result  Correct absence of result
```

Fig. 8 (prior art)

SYSTEM AND METHOD FOR ASSESSING WOUND

CROSS REFERENCE TO RELATED APPLICATIONS

This application claims priority to and benefit of U.S. Provisional Application No. 61/897,559, entitled SYSTEM AND METHOD FOR ASSESSING WOUND, filed on Oct. 30, 2013, and of U.S. Provisional Application No. 61/898,907, entitled SYSTEM AND METHOD FOR ASSESSING WOUND, filed on Nov. 1, 2013, both of which are incorporated by reference herein in their entirety and for all purposes.

STATEMENT REGARDING FEDERALLY SPONSORED RESEARCH OR DEVELOPMENT

This invention was made with government support under Grant No. IIS-1065298, awarded by the National Science Foundation (NSF). The federal government may have certain rights in the invention.

BACKGROUND

The present teachings relate to a system and a method for assessing chronic wound. More particularly, the present teachings relate to a system and a method for assessing wound for patients with, for example, type 2 diabetes and diabetic foot ulcers. One way to assess wound is to use a specialized camera to capture the wound image, then calculates the wound area and organizes wound images from different patients and stores images in a central location. Another way to assess wound is to use a mobile wound analyzer (MOWA), which is an Android-based software, intended for smart phones and tablets, for analysis of wound images. The wound boundary needs to be traced manually after which the software calculates the wound area and performs color analysis within the wound boundaries.

The conventional art does not address the problem of capturing foot images when the patients with diabetes have limited mobility. In addition, the prior art device is very costly and not affordable for individual patients to own, apart from MOWA, which, however, is designed for clinicians. Further, the prior art is not designed for joint use by both the patient and his/her doctor, through automatic upload of raw and analyzed wound images to cloud storage for easy access by the physician. Accordingly, there is a need to develop new system and method for assessing wound that overcome the above drawbacks in the prior art.

BRIEF SUMMARY

The present teachings provide patients with diabetes and chronic foot ulcers an easy-to-use and affordable tool to monitor the healing of their foot ulcers via a healing score; at the same time, the patient's physician can review the wound image data to determine whether intervention is warranted. The system is also applicable for patients with venous leg ulcers.

In accordance with one aspect, the present teachings provide a method for assessing wound. In one or more embodiments, the method of these teachings includes capturing an image of a body part including the wound area, analyzing the image to extract a boundary of the wound area, performing color segmentation within the boundary, wherein the wound area is divided into a plurality of segments, each segment being associated with a color indicating a healing condition of the segment and evaluating the wound area.

In accordance with another aspect, the present teachings provide a system for assessing wound. In one or more embodiments, the system of these teachings includes an image acquisition component configured to capture an image of a body part including a wound area, an image analysis module configured to extract a boundary of the wound area; an image segmentation module configured to perform color segmentation within the boundary of the wound area, wherein the wound area is divided into a plurality of segments, each segment being associated with a color indicating a healing condition of the segment and a wound evaluation module configured to evaluate the wound area.

A number of other embodiments of the method and system of these teachings are presented herein below.

For a better understanding of the present teachings, together with other and further needs thereof, reference is made to the accompanying drawings and detailed description and its scope will be pointed out in the appended claims.

BRIEF DESCRIPTION OF THE DRAWINGS

FIG. 8 shows the conventional confusion matrix that is used in these teachings;

FIGS. 12a-12c are graphical representations of a component of one embodiment of the system of these teachings;

DETAILED DESCRIPTION

Figure 1:
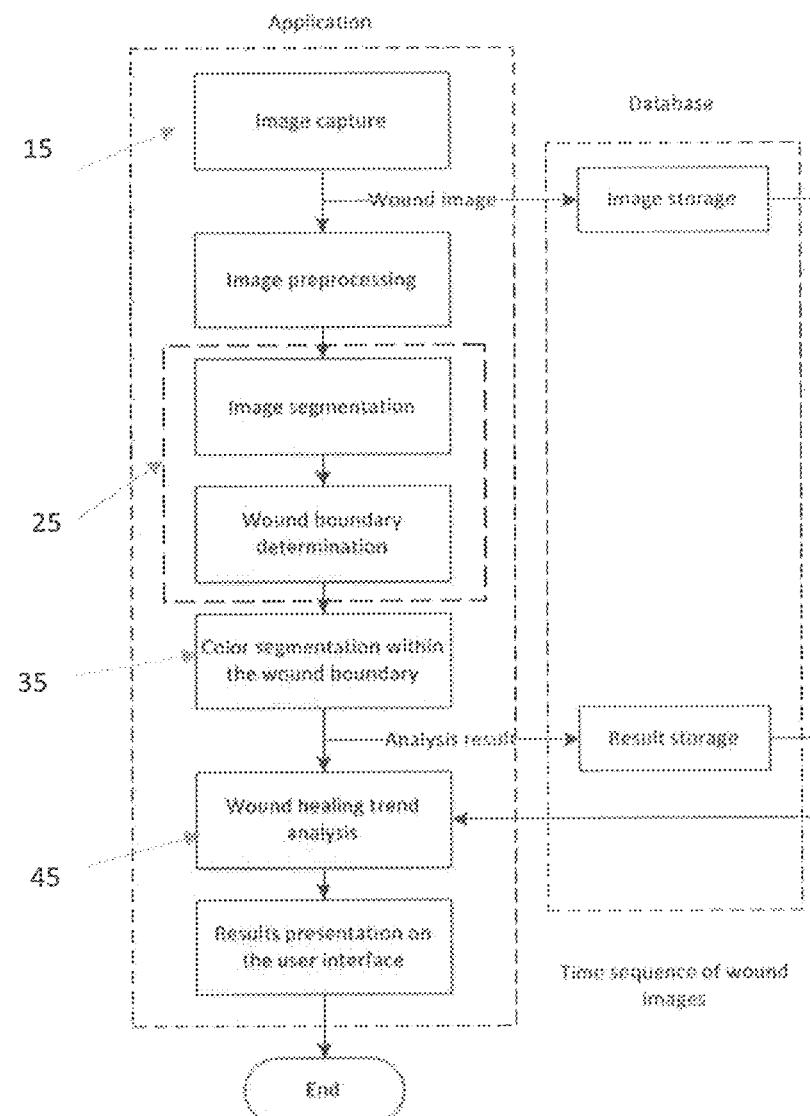
FIG. 1 represents a schematic block diagram representation of one embodiment of the system of these teachings.

The following detailed description is not to be taken in a limiting sense, but is made merely for the purpose of illustrating the general principles of these teachings, since the scope of these teachings is best defined by the appended claims. Although the teachings have been described with respect to various embodiments, it should be realized these teachings are also capable of a wide variety of further and other embodiments within the spirit and scope of the appended claims.

As used herein, the singular forms "a," "an," and "the" include the plural reference unless the context clearly dictates otherwise.

Except where otherwise indicated, all numbers expressing quantities of ingredients, reaction conditions, and so forth used in the specification and claims are to be understood as being modified in all instances by the term "about."

In the following, the term "handheld mobile communication device," as used herein, refers to a device capable of being handheld and of executing applications, and which is portable. In one instance, the mobile communication device has one or more processors and memory capability. Examples of mobile communication devices, these teachings not being limited to only these examples, include smart mobile phones, digital personal assistants, etc.

The present teachings relate to a wound image analysis system, which may be implemented as hardware and/or software. In one embodiment, the wound image analysis system of the present teachings is designed to operate on a handheld mobile communication device, such as a smart phone. The wound image analysis system may be used in private homes or elder care facilities by the patient him/herself, or in collaboration with a caregiver, with the relevant image data automatically uploaded to secure cloud storage, to be accessible for perusal by the patient's doctor and/or clinicians in the patient's wound clinic. An alert system can notify the patient's doctor if wound data exceeds some preset bounds. In another embodiment, the wound image analysis system of the present teachings may operate in a wound clinic and cover several patients. In this embodiment, a smart phone is use collaboratively with a laptop (i.e., a smart phone-laptop collaborative system).

In one embodiment, the wound image analysis method of the present teachings includes the following main parts: (i) image preprocessing, (ii) method for determining the wound boundary, (iii) method for color image segmentation, (iv) method for computing the healing score. In other embodiments, the system of these teachings component configured to determine the wound boundary, configured to perform color image segmentation and component configured to assess the wound area. Other embodiments of the system of these teachings also include an image capture box to aid the patient and/or his/her caregiver in capturing images of the foot ulcer under controlled distance and light conditions, and cloud storage and clinical access solution. Each of these components will be described briefly below, with additional details given in the attached documents. While each system component is essential for the functionality of the system, not all components are necessary to operate the wound image analysis system.

(i) Image pre-processing. A JPEG image captured by a smart phone is converted into an RUB bitmap image. An image noise reduction filter is applied to down-sample the image for faster processing.

(ii) Component configured to determine the wound boundary. The wound boundary detection method is based on the mean shift segmentation of the wound image. The method first detects the outline of the foot and then within the boundary of the foot locates the outline of the wound. A more accurate method may be used for wound boundary detection based on skills and insight by experienced wound clinicians. For this purpose, machine learning methods, such as the Support Vector Machine, may be used to train the wound analysis system to learn about the essential features about the wound.

(iii) Component configured for color image segmentation. The color segmentation method is instrumental in determining the healing state of the wound where red indicates healing, yellow indicates inflamed, and black indicates necrotic.

(iv) Component configured to compute a healing score. The Healing Score is an important element of communicating in a simple fashion the healing status of the patient's wound. The Healing Score is a weighted sum of factors, such as: wound area; weekly change in wound area; wound texture; relative size and shapes of the healing, inflamed and necrotic regions within the wound boundary, and possibly the skin color around the wound. The weighing factors are determined from expert clinical input.

(v) Image capture box. The image capture box is a device that allows a patient, possibly with the aid of his/her caregiver, to both visually observe the appearance of a wound on the sole of the foot as well as capture an image of the wound for storage and analysis. It is a compact box, where the patient's foot can rest comfortably on a 45' angled surface next to the smart phone holder. The angled surface can readily be flipped to accommodate right foot as well as left foot. The box contains two front surface mirrors and warm white LED lighting.

(vi) Cloud storage and clinical access solution. The cloud storage and clinical access solution automatically uploads relevant wound data to the cloud (e.g., network accessible storage) from the smart phone, either utilizing Wi-Fi (802.11), 3G, or other wireless network. Relevant data comprises wound image data, which is automatically uploaded in encrypted form to secure cloud storage, to be accessible for perusal by the patient's doctor. An alert system can alert the doctor if wound data exceeds some preset bounds.

In another embodiment, the wound image analysis system operates in a wound clinic and covers several patients. In this embodiment, a handheld mobile communication device-Computing Component collaborative system is used, in which a captured image is automatically transferred to a computing component, in one instance, the transfer occurs through a peer-to-peer based Wi-Fi system or Local Area Network, using a wired or wireless router.

Moreover, in a further embodiment, instead of using the smart phone camera as the image acquisition device, the wound image analysis system can use a compact hyperspectral camera integrated into the image capture box. In one instance, three types of LED illumination are integrated into the image capture box: infrared (IR) LED illumination; visible light illumination, using the already built-in warm white LED illumination; and ultraviolet (UV) LED illumination. This allows the wound to be imaged by three distinct wavelength bands, with the expectation of revealing much better diagnostic information about the wound. In one instance, The hyperspectral camera includes direct communication capability, such as but not limited to by which the captured images are transmitted to a device, such as a handheld mobile communication device or a computing device, for processing and cloud upload.

In accordance with one aspect, the present teachings provide a method for assessing wound. In one or more embodiments, the method of these teachings includes capturing an image of a body part including a wound area, analyzing the image to extract a boundary of the wound area, performing color segmentation within the boundary, wherein the wound area is divided into a plurality of segments, each segment being associated with a color indicating a healing condition of the segment and evaluating the wound area.

In one or more embodiments, the system of these teachings includes an image acquisition component configured to capture an image of a body part including a wound area, an image analysis module configured to extract a boundary of the wound area; an image segmentation module configured to perform color segmentation within the boundary of the wound area, wherein the wound area is divided into a plurality of segments, each segment being associated with a color indicating a healing condition of the segment and a wound evaluation module configured to evaluate the wound area.

One embodiment of the system of these teachings is shown in FIG. 1. Referring to FIG. 1, in the embodiment shown there in, an image capture component 15 captures the image, the image is preprocessed and provided to an image analysis component 25 that is configured to extract a boundary of the area of the wound. An image segmentation component 35 is configured to perform color segmentation on the image within the wound boundary. In the color segmentation the area of the image within the one boundary is divided into a number of segments, each segment being associated with the color that indicates a healing condition of the segment. A wound evaluation component 45 receives the information from the image segmentation component 35 and provides an analysis of the wound healing trend.

In one instance, after the wound image is captured, the JPEG file path of this image is added into a wound image database. This compressed image file, which cannot be processed directly with the main image processing algorithms, therefore needs to be decompressed into a 24-bit bitmap file based on the standard RGB color model. In one instance, the built-in APIs of the smartphone platform to accomplish the JPEG compression and decompression task. The "image quality" parameter is used to control the JPEG compression rate. In one embodiment, setting "image quality" to 80 was shown empirically to provide the desirable balance between quality and storage space. In that embodiment, for an efficient implementation on the smartphone alone, no method was used to further remove the artifacts introduced by JPEG lossy compression.

In one instance, in the Image preprocessing step, the high resolution bitmap image is first down-sampled to speed up the subsequent image analysis and to eliminate excessive details that may complicate the wound image segmentation. In one instance, the original image (pixel dimensions 3264× 2448) is down-sampled by a factor 4 in both the horizontal and vertical directions to pixel dimensions of 816×612, which has proven to provide a good balance between the wound resolution and the processing efficiency. Afterwards, the images is smoothed to remove noise (assumed mainly to be Gaussian noise produced by image acquisition process) by using the Gaussian blur method whose standard deviation σ=0.5 was empirically judged to be substantially optimal based on multiple experiments.

In one or more instances, in the method of these teachings, analyzing the image includes performing mean shift segmentation and object recognition and, in the system of these teachings, the image analysis component is configured to perform mean shift segmentation and object recognition. In the mean shift based image segmentation and region merge operations, the wound boundary determination task doesn't rely on any clinical inputs. The Foot outline detection is accomplished by finding the largest connected component in the segmented image. Afterwards, a wound boundary determination was carried out based on the smart analysis of previous foot outline detection result. This solution is very efficient and easy to be implemented on the handheld mobile communication device platform. However, the toe-amputation status has to be recorded as part of patients' data.

Basic Mean Shift Method

Many non-parametric clustering methods can be separated into two parts: hierarchical clustering and density estimation. Hierarchical clustering is a method of cluster analysis, which seeks to build a hierarchy of clusters. Strategies for hierarchical clustering generally fall into two types including 1) agglomerative: this a "bottom up" approach in which each observation starts in its own cluster and pairs of clusters are merged as one moves up the hierarchy; 2) divisive: this is a "top down" approach in which all observations start in one cluster and splits are performed recursively as one moves down the hierarchy. On the other hand, the concept of the density estimation-based non-parametric clustering method is that the feature space can be considered as the experiential probability density function of the represented parameter. The mean shift algorithm can be classified as density estimation. It adequately analyzes feature space to cluster them and can provide reliable solutions for many vision tasks.

In general, the mean shift algorithm models the feature vectors associated with each pixel (e.g., color and position in the image grid) as samples from an unknown probability density function $f(x)$ and then try to find clusters (dense areas) in this distribution. The key to mean shift is a technique for efficiently finding peaks in this high-dimensional data distribution (In these teachings, there will be 5 dimension including 3 color range dimension and 2 spatial dimension) without ever computing the complete function explicitly. The problem is simplified to how to find the local maxima (peaks or modes) in an unknown density distribution. Let us take a look at the kernel density estimation definition at first. Given n data points $x_i$, i=1, . . . , n in the d-dimensional space $R^d$, the multivariate kernel density estimator with kernel K(x) is shown as below (see D. Comdniciu, P. Meer, Mean Shift: A Robust Approach Toward Feature Space Analysis, IEEE Tran. on Pattern Analysis and Machine Intelligence, vol 24 (5), May 2002, pp. 603-619, which is incorporated by reference herein is entirety and for all purposes).

$$f(x) = \frac{1}{nh^d} \sum_{i=1}^{n} K\left(\frac{x - x_i}{h}\right) \qquad \text{Eq. 3.1}$$

where h is one bandwidth parameter satisfying h>0 and K is the radially symmetric kernels satisfying $$K(x) = c_{k,d} k(\|x\|^2) \qquad \text{Eq. 3.2}$$

where $c_{k,d}$ is a normalization constant which makes K(x) integrate to one. The function k(x) is the profile of the kernel, defined only for x≥0. After applying the profile notation, the density estimator in Eq. 3.1 can be written as below [32].

$$f_{h,K}(x) = \frac{c_{k,d}}{nh^d} \sum_{i=1}^{n} k\left(\left\|\frac{x-x_i}{h}\right\|^2\right) \quad \text{Eq. 3.3}$$

In mean shift algorithm, a variant of what is known in the optimization literature is used as multiple restart gradient descent. Starting at some guess for a local maxima $y_k$, which can be a random input data point $x_i$, mean shift computes the density estimate $f(x)$ at $y_k$ and take a uphill step in the gradient descent direction. The gradient of $f(x)$ is given by $$\nabla f(x) = \frac{2c_{k,d}}{nh^{d+2}} \sum_{i=1}^{n} (x_i - x) g\left(\frac{\|x_i - x\|^2}{h^2}\right) \quad \text{Eq. 3.4}$$

where g(r)=-k'(r) and n is the number of neighbors taken into account in the 5 dimension sample domain. In one instance, the Epanechinikov kernel shown as Eq. 3.2 is used, which makes the derivative of this kernel is a unit sphere. If the Eq. 3.4 is rewritten as the following $$\nabla f(x) = \frac{2c_{k,d}}{nh^{d+2}} \left[\sum_{i=1}^{n} g\left(\left\|\frac{x-x_i}{h}\right\|^2\right)\right] \times m(x) \quad \text{Eq. 3.5}$$

$$m(x) = \frac{\sum_{i=1}^{n} x_i g\left(\left\|\frac{x-x_i}{h}\right\|^2\right)}{\sum_{i=1}^{n} g\left(\left\|\frac{x-x_i}{h}\right\|^2\right)} \quad \text{Eq. 3.6}$$

The vector in Eq. 3.6 is called the mean shift vector, since it is the difference between the weighted mean of the neighbors $x_i$ around x and the current value x. In the mean-shift procedure, the current estimate of the mode $y_k$ at iteration k is replaced by its locally weighted mean as shown below:

$$y_k = y_k + m(y_k) \quad \text{Eq. 3.7}$$

This iterative update of the local maxima estimation will be continued until the convergence condition is met. In one instance, the convergence condition is set as the Euclidean length of the mean shift, vector is smaller than a preset threshold.

Actually, in the mean shift based algorithm as used in these teachings, the mean shift update thread is performed multiple times by taking each pixel in the image plane as the starting point and replace the current pixel with the converged local maxima point. All the pixels leading to the same local maxima will be set as the same label in the label image. After this, the very first mean shift segmentation (strictly speaking, it is the mean shift smooth filtering) result is obtained while it is almost definitely over-segmented. Therefore, the over-segmented image has to be merged based on some rules. In the fusion step, extensive use was made of region adjacency graphs (RAG).

Figure 2A:
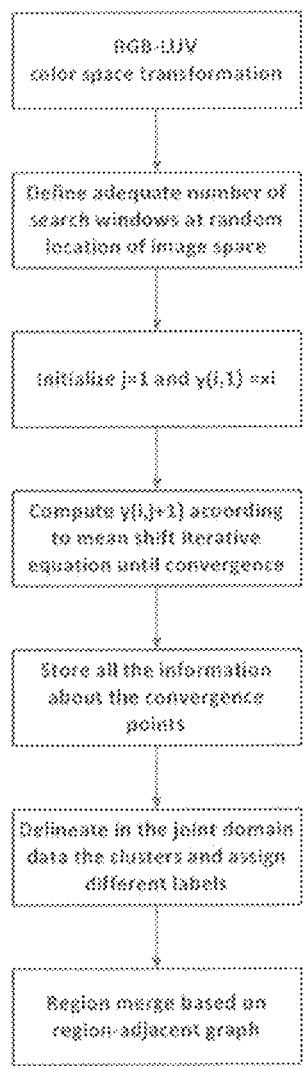
FIG. 2a is a flowchart representation of the mean shift based segmentation algorithm as used in these teachings.

The method flowchart is shown as in FIG. 2a. The reason for using the LUV color space is because that perceived color differences should correspond to Euclidean distances in the color space chosen to represent the features (pixels). The LUV and LAB color space were especially designed to best approximate uniformly color space. To detect all the significant modes, the following basic mean shift filtering process should be run for multiple times (evolving in principle in parallel) with different starting points that cover the entire feature space. In these teachings, all the pixels in the image domain are used as the starting points.

The first step in the mean shift based feature space with the underlying density $f(x)$ is to find the modes of this density. The modes are located among the zeros of the gradient $\nabla f(x)=0$, and the mean shift procedure is an elegant way to locate these zeros without estimating the density completely. The mean shift vector m(x) computed in Eq. 3.6 with kernel g is proportional to the normalized density gradient estimate obtained with kernel k. In Eq. 3.6, "n" represents the number of neighbor pixels $x_i$ involved in the kernel density estimation see, for example, C. M. Christoudias, B. Georgescu, P. Meer, Synergism in Low Level Vision, IEEE Proc. of $16^{th}$ Inter. Conf. on Pattern Recognition, 2002, Vol. 4: pp. 150-155, which is incorporated by reference herein is entirety and for all purposes). All the neighbor pixels located within the Euclidean distance h from the current pixel will be chosen. The mean shift vector thus always points toward the direction of the maximum increase in the density. In this case, the $y_k$ is iteratively updated according to Eq. 3.7 until the convergence will lead to the local maxima for the current point in the probability density function (PDF). The convergence is defined as when the difference between $y_k$ and $y_{k+1}$ is smaller than a specified threshold value.

In Eq. 3.6, "i" represents the $i^{th}$ gradient descent path. After all the local maxima have been detected from different starting points, all the points on the path leading to each maxima will be claimed to belong to the basin marked by the current maxima. Then the basins with the size smaller than the pre-stetting threshold value will be merged to the nearest basin whose size is bigger than a preset threshold. In both equations, the pixel is described by a 5 dimension vector concatenated in the joint spatial-range domain including 3 elements for the LUV color domain and 2 elements for the spatial domain. As stated hereinabove, the kernel function k is chosen as the Epanechinikov kernel. In these teachings, the combined kernel function shown in Eq. 3.8 is used.

$$K_{hs,hr}(x) = \frac{C}{hs^2 hr^3} k\left(\left\|\frac{x^s}{hs}\right\|^2\right) k\left(\left\|\frac{x^r}{hr}\right\|^2\right) \quad \text{Eq. 3.8}$$

where hs and hr are different bandwidth values for spatial domain and range domain, respectively.

After the initial mean shift filtering procedure, the over-segmented image are merged based on some rules. In the fusion step, extensive use was made of region adjacency graphs (RAG). The initial RAG was built from the initial over segmented image, the modes being the vertices of the graph and the edges were defined based on 4-connectivity on the lattice. The fusion was performed as a transitive closure operation on the graph, under the condition that the color difference between two adjacent nodes should not exceed hr/2.

Mean Shift Based Segmentation

Figure 2B:
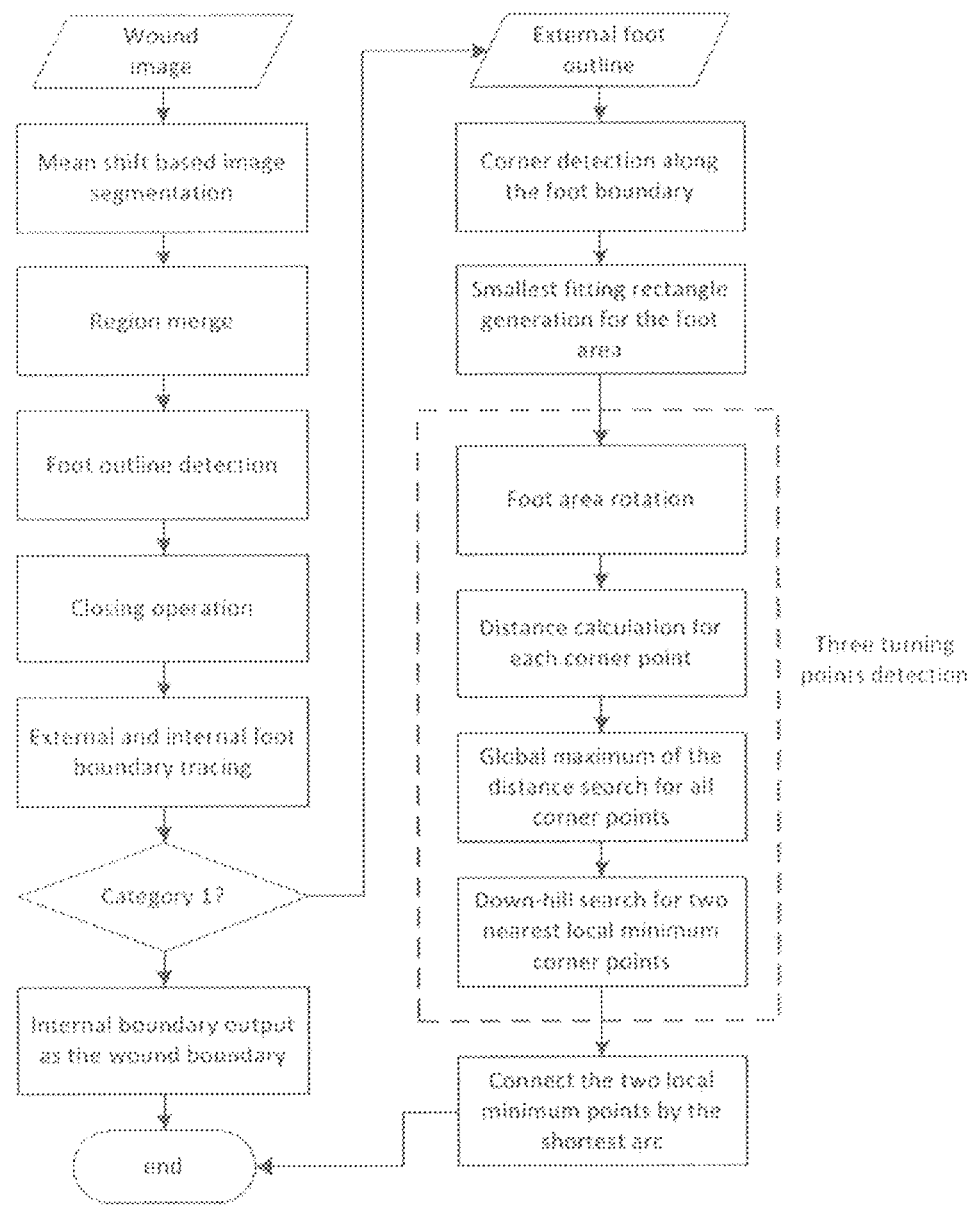
FIG. 2b is a flowchart representation of the mean shift based method for wound boundary determination as used in these teachings.
Figure 3A:
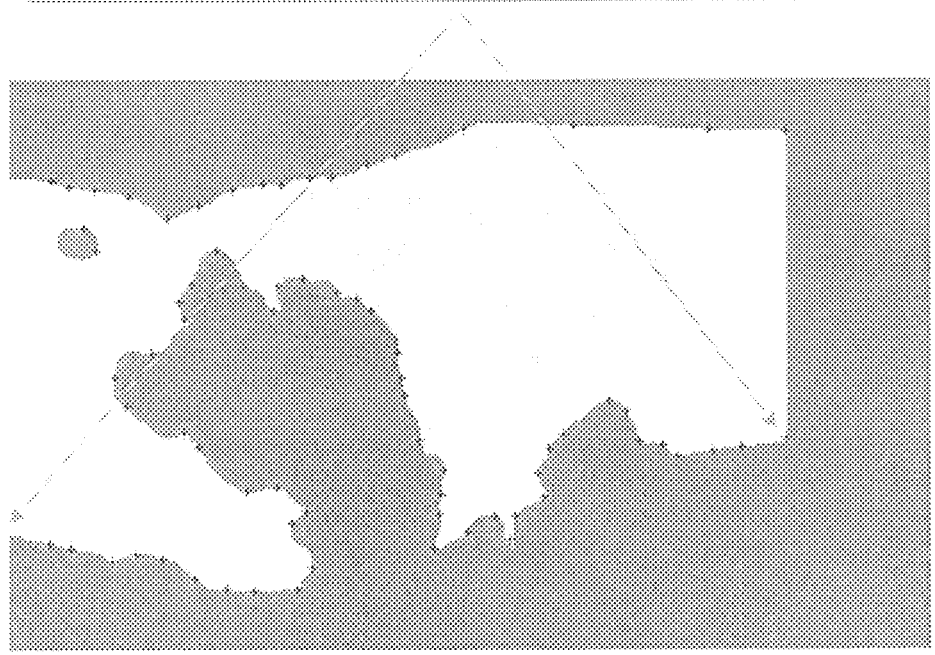
FIGS. 3a-3d are results of different operations in the wound boundary determination of these teachings.
Figure 3B:
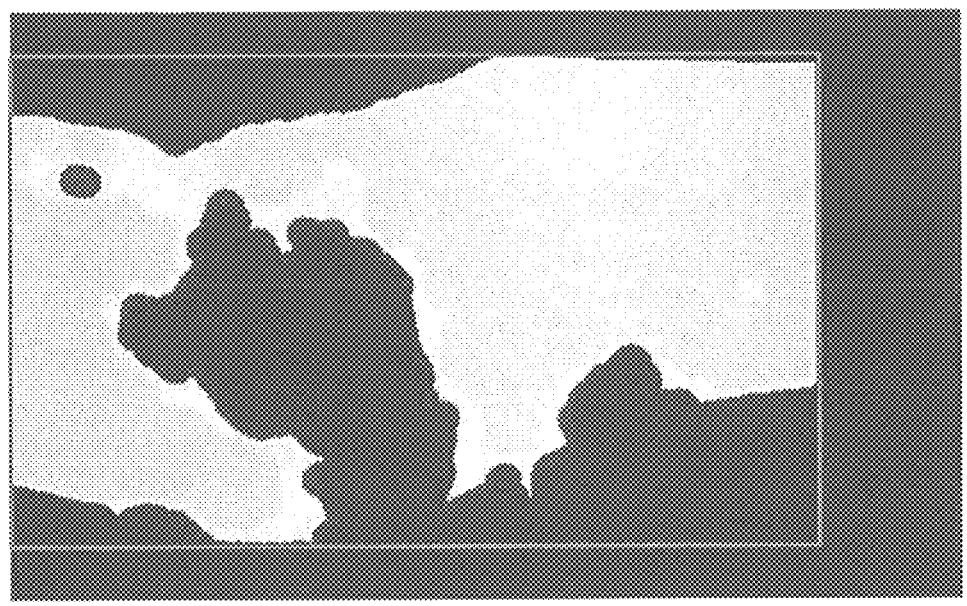
Figure 3C:
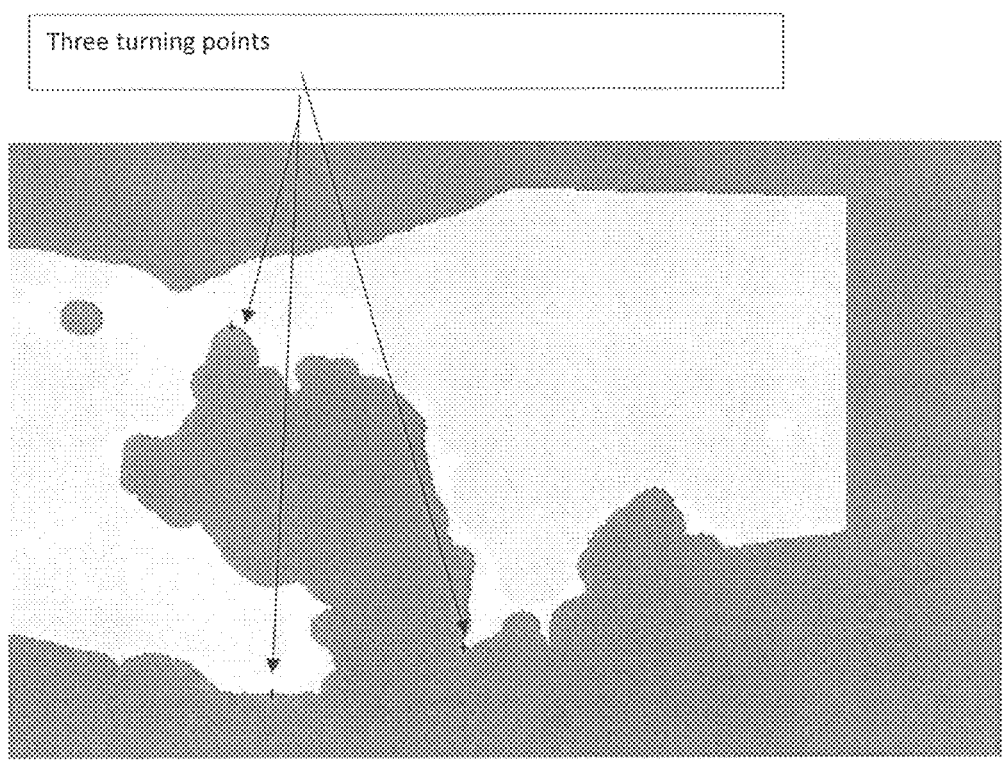
Figure 3D:
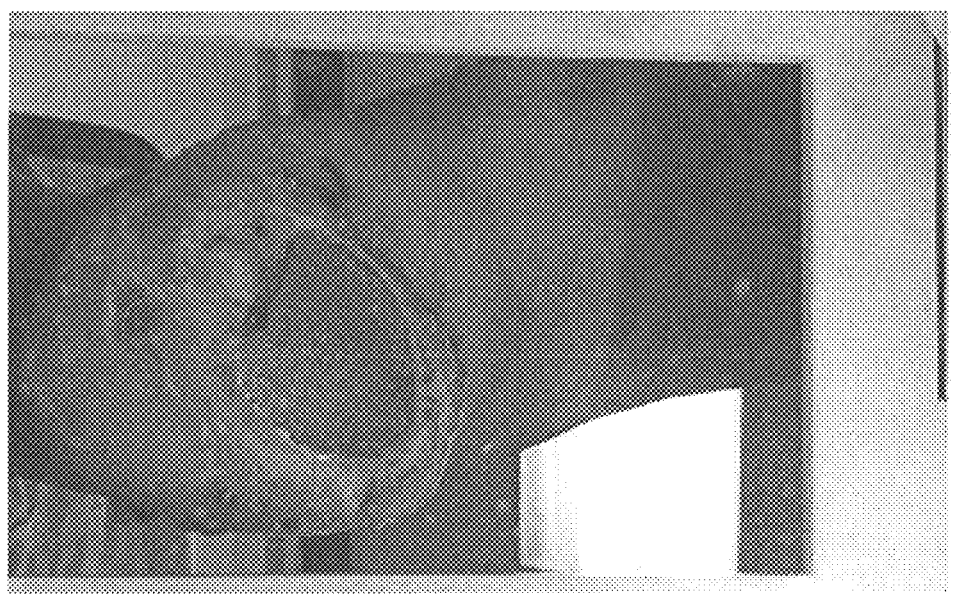

The wound boundary determination approach using mean shift based segmentation is theoretically full-automatic and does not depend on any a priori manual input, which makes it computationally very economic and flexible for implementation in any hardware platforms. In FIG. 2b, the workflow of this approach is provided.

The mean shift based algorithm is first applied to segment the original wound image into a number of homogeneous regions. The mean shift algorithm is chosen over other segmentation methods, such as level set and graph cut based algorithms for several reasons. First, the mean shift algorithm takes into consideration the spatial continuity inside the image by expanding the original 3D color range space to 5D space, including two spatial components, since direct classification on the pixels proved to be inefficient. Second, a number of acceleration algorithms are available. Third, for both mean shift filtering and region merge methods, the quality of the segmentation is easily controlled by the spatial and color range resolution parameters. Hence, the segmentation algorithm can be adjustable to different degrees of skin color smoothness by changing the resolution parameters. Finally, the mean shift filtering algorithm is suitable for parallel implementation since the basic processing unit is the pixel. In this case, the high computational efficiency of GPUs can be exploited, which can further improve the efficiency and achieve the real time wound assessment even on the smartphone-alone system.

After applying the mean shift algorithm, the image is usually over-segmented, which means that there are more regions in the segmentation result than necessary for wound boundary determination. To solve this problem, the over-segmented image is merged into a smaller number of regions which are more object-representative based on some rules. In the fusion step, extensive use was made of region adjacency graphs (RAG). The initial RAG was built from the initial over-segmented image, the modes being the vertices of the graph and the edges defined based on 4-connectivity on the lattice. The fusion was performed as a transitive closure operation on the graph, under the condition that the color difference between two adjacent nodes should not exceed $h_f$, which is regarded as the region fusion resolution. Based on experimental results, the over-segmentation problem is found to be effectively solved by region fusion procedure.

Foot Outline Detection and Task Categorization

The wound boundary determination method is based on two assumptions. First, the foot image contains little information not related to the chronic wound. In reality, it is not a critical problem as it is assumed that the patients and/or caregivers will observe the foot image with the wound on the smartphone screen before the image is captured to ensure that the wound is clearly visible. Second, it is assumed that the healthy skin on the sole of the foot is a nearly uniform color feature.

The largest connected component detection is first performed on the segmented image, using the fast largest connected component detection method including two passes. In the processing step Foot Color Thresholding, the color feature, extracted in the mean shift segmentation algorithm of this component, is compared with an empirical skin color feature by calculating the Euclidean distance between the color vector for the current component and the standard skin color vector from the Macbeth color checker. If the distance is smaller than a pre-specified and empirically determined threshold value, the foot area is considered as having been located. Otherwise, the largest component detection algorithm is iteratively repeated on the remaining part of the image while excluding the previously detected components until the color threshold condition is satisfied. After the foot area is located, a binary image is generated with pixels that are part of the foot labeled "1" (white) and the rest part of the image labeled "0" (black).

Then, the wound boundary determination tasks have to be classified into two categories: 1) the wound is fully enclosed within the foot outline; 2) the wound is located at (or very near to) the boundary of the foot outline. The initial idea was to use the foot boundary smoothness to distinguish between these two situations. However, the problem is that a gold standard for the ordinary smooth foot curve may be needed, i.e. the boundary of the healthy foot, and quantitatively compare the actually detected foot outline to it in some way. The search for such a ground truth healthy foot curve is never an easy task. Moreover, it has to be ensured that the patient's entire foot is imaged completely, which is a difficult-to-meet expectation for a self-management wound analysis system considering the possible low mobility and the lack of experience of handheld communication device use for most type 2 diabetic patients. Therefore, the following method is used to realize the task classification.

At first, one of the image morphology operations called a closing operation (with a 9×9 circle structure element) is applied to remove all the holes in the foot region (white part in the binary image) and smooth the external foot boundary, which will help us to eliminate the possible interference for accurate wound boundary determination. Secondly, the combined region and boundary algorithm is applied to trace the external foot boundary along the edge of the white part in the foot binary image, as well as all the internal boundaries if there are any. For all the internal boundaries in a foot region, only the ones with the perimeter larger than a preset threshold (in one embodiment, it is set as 50 pixel lengths) are kept. This simple threshold method may not be a perfect algorithm but it works for most of the wound images in many instances. In other words, if there is at least one internal boundary exceeding the preset threshold within the foot region, it is regarded as the wound boundary and returns it as the final boundary determination result. On the other hand, if there are not any internal boundaries whose length are beyond the threshold, other boundary determination methods may be needed. Note that here it is assumed there is at least one wound area on the photographed foot.

Boundary Determination for the Wounds Near the Edge of the Foot Outline

After a careful study and observation, a wound boundary determination method, as shown in the right column in FIG. 2b, is used that is applicable for a wound located at or near to the foot outline. As stated herein above, the external boundary of the non-enclosed foot outline is already available.

As illustrated in the block diagram in FIG. 2b, the input to this method is the external boundary. Instead of keeping all the points on the foot boundary, the edge points (all the points on the external boundary of the foot region) are down-sampled by applying the Harris Corner Detection method to a number of corner points (as shown in part (a) of FIG. 3). The corner points, also called junctions of edges, are prominent structural elements in an image and are therefore useful in a wide variety of computer vision application. It is claimed that corner points are more robust features for geometric shape detection than the regular edge points. In one instance, the perimeter of the foot outline usually is made up of over 2000 pixels. After down sampling by corner detection, the number of corner points is approximately around 60-80 (also in terms of pixels). This will greatly improve the time efficiency of the algorithm. Besides, this down-sampling procedure will also benefit us when detecting the turning points (this will be discussed in detail in herein below).

The third to the eighth blocks in the right column in FIG. 2b shows the main idea, which is to detect the three turning points on the foot boundary. These turning points will be used to determine the wound section on the foot outline (shown in the part (c) of FIG. 3 by marking the three turning points with small black crosses). The turning points can be defined as the most abruptly changing points along the foot boundary. After the three points are determined, one can move along from the global maximum point (which is the most concave point in the middle) to the two local minimum points along the foot boundary in two opposite directions. Then the two local minimum points are connected by an arc which is the substantially optimal approximation to the non-closed part of the wound boundary. In one instance, an arc is drawn from either local minimum to the other one with a radius equal to half of the diagonal length for the wound image. The trace generated by the above two steps is the target wound boundary (as shown by a red curve in FIG. 3d).

For detecting the turning points, a maximum-minimum searching approach is used to detect the turning points. Herein below, a detailed description of this approach is provided.

Figure 4A:
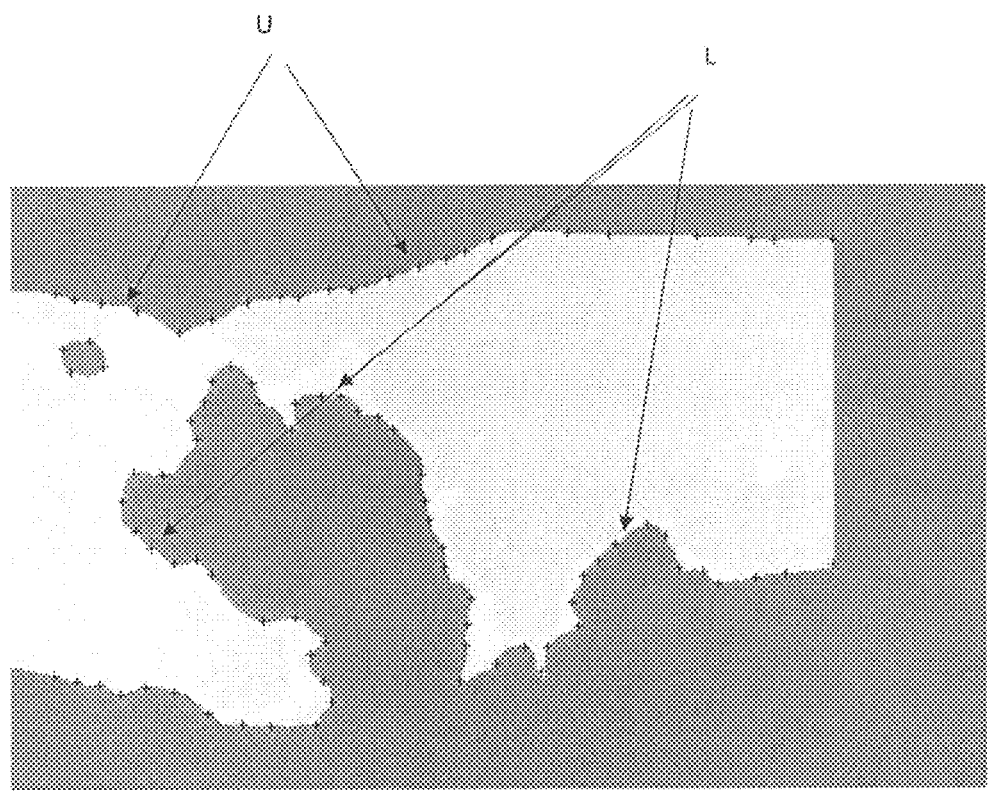
FIGS. 4a-4c are results in the calculation of wound location of these teachings.

First, all the corner points are sorted into a list based on their position on the foot boundary (from the top-right to top-left, in a clock-wise direction), then locate the two special extreme corner points on the foot boundary: the leftmost and the rightmost (as indicated in part (a) of FIG. 3). Then, the corner points are divided into two groups: the corners points which located between the two extreme points and the corner points located outside this range. Note that this categorization is based on the clockwise sorted corner points list. In FIG. 4a, the first group of corner points is marked by U and the second group is marked by L. For the first group the vertical distance of each corner point to the top side of the Smallest Fitting Rectangle (SFR) of the foot region is calculated. The smallest fitting rectangle is supposed to be tangent to the foot area at four boundary points: the top-most, bottom-most, left-most and right most point of the foot area, as shown by the frame in FIG. 4b.

Figure 4B:
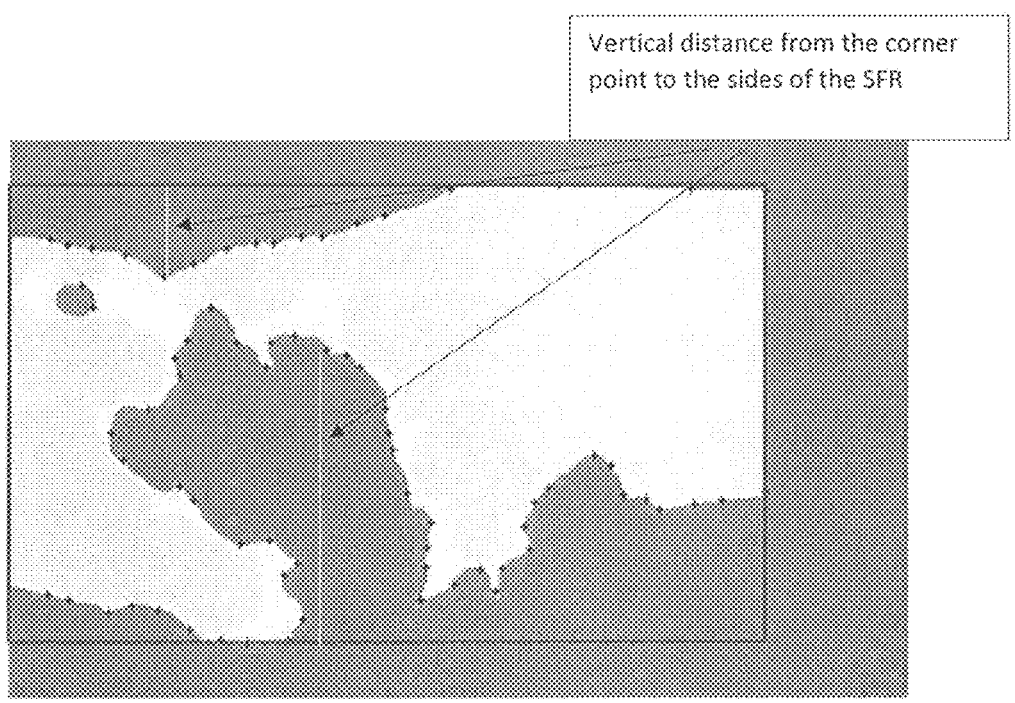
Figure 4C:
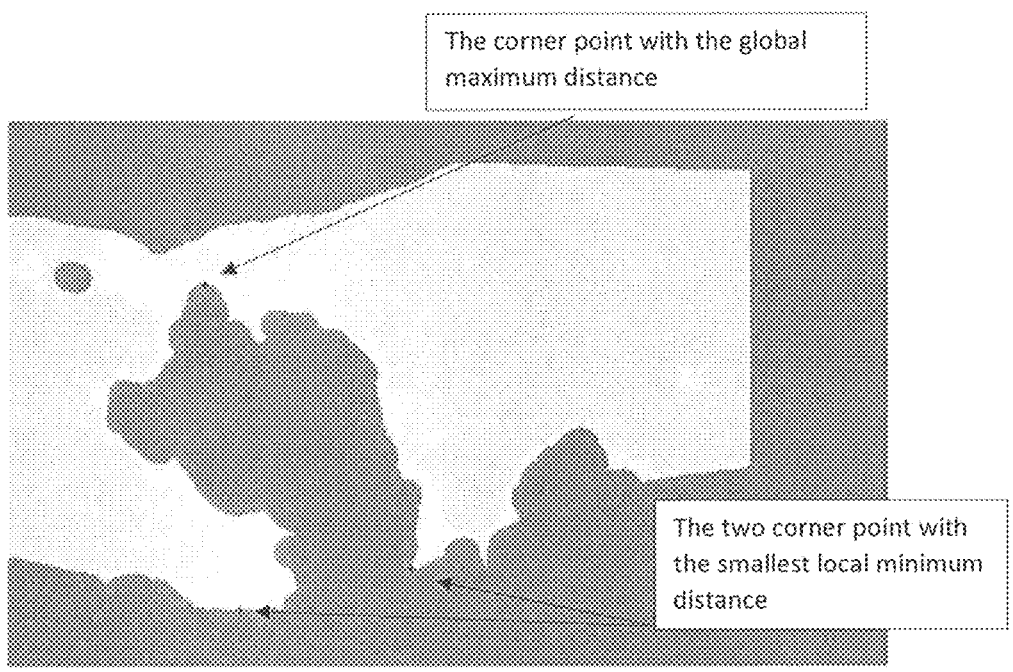

Similarly, the vertical distance of each corner point in the second group to the bottom side of the SFR (as shown in FIG. 4b) is calculated. Afterwards, the turning points are located by seeking for the corner point with global maximum vertical distance to the corresponding rectangle side (top or bottom based on its group number: first or second) and also two corner points on each side of the maximum point with the smallest local minimum vertical distance (as shown FIG. 3c). The only concern is the search for target turning points may be accidentally stopped by interfering local extrema, which is a common problem of most local search algorithms. As stated above, a certain number of corner points are kept on the foot outline. Based on experimental results, it is found that this down-sampling procedure can eliminate most of the interfering local extrema which may impede the search for the optimal turning points.

The above disclosed method mainly classifies the wound locations into three categories: 1) wound in the middle of the foot, 2) wound at the edge of the foot without toe-amputation and 3) wound at the edge of the foot with toe-amputation. For the first category, the wound is supposed to be surrounded by healthy skin and can be easily detected by tracing the internal boundary within the foot outline. For the second and third categories, the three turning points detection method is applied to locate the wound boundary which is assumed to be the most irregularly changed section on the foot outline. In practice, the method dealing with these two situations (with or without toe-amputation) is slightly different. Hence, the toe-amputation information may need to be given as an input to the method and obtained as part of the patient's medical information.

In another instance, in the method of these teachings, analyzing the image includes using a trained classifier and, in the system of these teachings, the image analysis component is configured to use a trained classifier.

A machine learning based solutions has been developed in which the wound boundary determination is an object recognition task since it is claimed that the machine learning (ML) is currently the only known way to develop computer vision systems that are robust and easily reusable in different environments. Herein below, the term "wound recognition" is used as the equivalent expression of "wound boundary determination", since both have the same goal.

In object recognition field, three major tasks needed to be solved to achieve the best recognition performance: 1) find the best representation to distinguish the object and background, 2) find the most efficient object search method and 3) design the most effective machine learning based classifier to determine whether a representation belongs to the object category or not.

For the Chronic wound recognition method and components of these teachings, a hybrid of the global window and local patch based representation which modifies the general form of the global texture descriptors to be extracted within only local sub-windows or patches is used. A popular approach of this hybrid type is called Bags of Visual Words (BoW) which uses a visual vocabulary to compactly summarize the local patch descriptors within a region using a simple 1D histogram (see, for example; (i) Fei-Fei Li; Perona, P., "A Bayesian Hierarchical Model for Learning Natural Scene Categories". 2005 IEEE Computer Society Conference on Computer Vision and Pattern Recognition (CVPR'05) p. 524 and (ii) Rob Fergus, Classical Methods for Object Recognition, slides presented at ICCV 2009 course, both of which are Incorporated by reference herein in their entirety and for all purposes).

This representation is completely orderless, which means that greater flexibility is allowed (for better or worse) with respect to viewpoint and pose changes. At the same time, the invariance properties of the individual local descriptors make them a powerful tool to tolerate the variation of the viewpoint or pose while giving informative local appearance cues. The regularity or rigidity of an object category's appearance pattern in 2D determines which style is better suited. For example, the class of frontal face is quite regular and similarity structured across instances, and thus is more suitable for the 2D layout-preserving descriptors; in contrast, wounds represent a variety of shapes of which most are irregular. This property makes it suited to a more flexible summary of the texture and key features. What is particularly convenient about the bag-of-words (BOW) representation is that it translates a (usually very large) set of high-dimensional local descriptors into a single sparse vector of fixed dimensionality across all images. This in turn allows one to use many machine learning algorithms that by default assume that the input space is vectorial—whether for supervised classification, feature selection, or unsupervised image clustering.

The object localization techniques can mainly fall into one of two categories: 1) the "top-down" technique, which tries to fit a coarse global object model to each possible location on the image grid or 2) the "bottom-up" technique, which tries to produce a pixel level segmentation of the input image and are built from the bottom up on learned local representation and can be seen as an evolution of texture detectors. The sliding window technique is a typical example for the first category. Due to its algorithmic nature, the sliding window search approach suffers from several limitations including the high computational cost, little room for error and inflexible for accurate wound boundary determination. Hence, in some related references, it is claimed the bottom-up technique is more suitable for object class segmentation task (similar as the wound boundary determination task).

The supervised learning methods have been most widely used. This approach will try to inferring a model from labeled training data. In related references, the comparison of several most popular supervised learning methods is provided. Generally speaking, support vector machine (SVMs) tends to perform much better when dealing with multi-dimensions and continuous features. (See, for example, Using Support Vector Machine as a Binary Classifier, International Conference on Computer Systems and Technologies—CompSysTech' 2005 which is incorporated by reference herein in its entirety and for all purposes). For SVMs, given a set of training examples, each marked as belonging to one of two categories, an SVM training algorithm builds a model that assigns new examples into one category or the other. An SVM model is a representation of the examples as points in space, mapped so that the examples of the separate categories are divided by a clear gap that is as wide as possible. New examples are then mapped into that same space and predicted to belong to a category based on which side of the gap they fall on. In addition to performing linear classification, SVMs can efficiently perform a non-linear classification using what is called the kernel trick, which implicitly mapping their linear inputs into high dimensional feature spaces.

Figure 5:
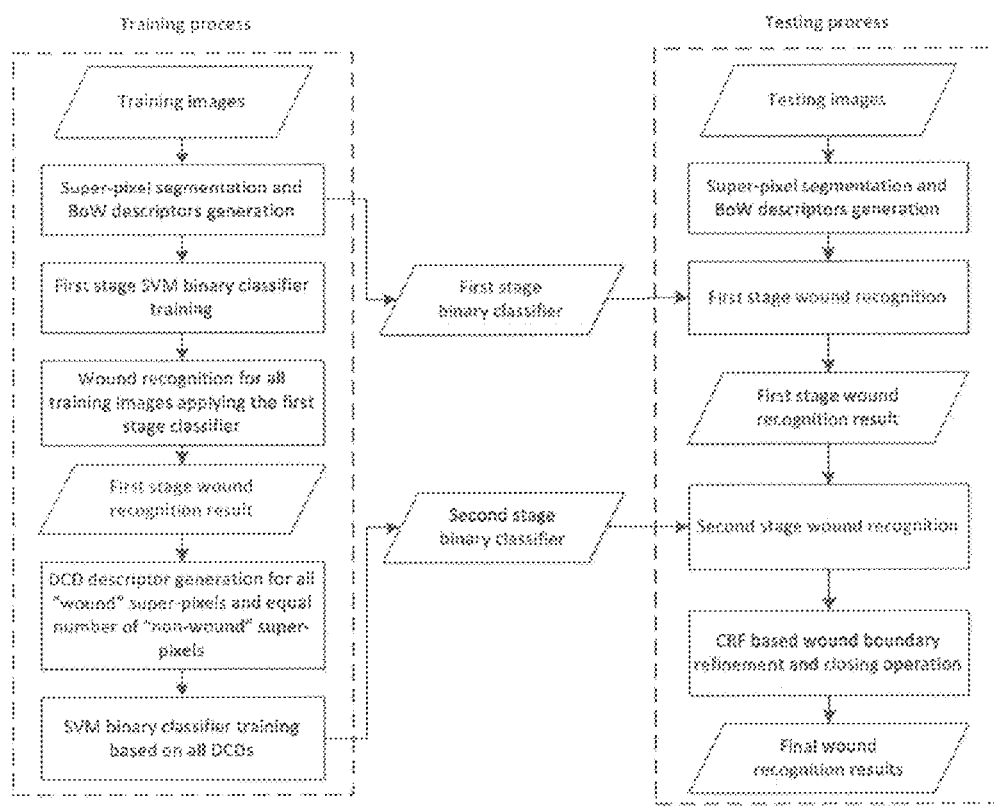
FIG. 5 is a flowchart representation of the machine learning based method for wound recognition of these teachings.

In one embodiment of these teachings, a two-stage recognition scheme based on some object recognition approach already being successfully applied in the pedestrian recognition task is used. The workflow of this wound recognition system is shown in FIG. 5.

In the training process, there are two stages. For both stages, the SVM based binary classifier training method is used. In the first stage, the super-pixel segmentation is performed by either the mean shift or SLIC (simply linear iterative clustering) algorithm to group pixels into perceptually meaningful atomic regions which can be used to replace the rigid structure of the pixel grid. Then, the vector representation is built up for each super-pixel by using the bag of words (BCW) histogram based on local DSIFT (dense SIFT) or SURF feature descriptor within the current super-pixel.

To generate this representation, the extracted descriptors are then quantized using a K-means dictionary and aggregated into one normalized histogram $h_i \in R_+^K$ for each super-pixel $s_i$ in the image, where K is the number of words predefined in the codebook (the set of clusters resulted from the K-means algorithm). In order to train a classifier, each super-pixel $s_i$ is assigned the most frequent class label it contains (in this case, some manually labeled ground truth images which have pixel-level granularity are needed). Then a SVM with an RBF kernel is trained on the labeled histograms for either category: wound and non-wound. This yields discriminant functions is proposed in relative references and shown as below.

$$C(h) = \sum_{j=1}^{L} c_i \exp(-\gamma d^2(h, h_i)) \quad (1)$$

where $c_i \in R$ are coefficients and $h_i$ representative histograms (support vectors) selected by SVM training, $\gamma \in R^+$ is a parameter selected by cross-validation, and $d^2(h, h_i)$ is the vector distance between the current histogram h and each support vector.

This classifier which results from this is very specific. It finds super-pixels which resemble super-pixels that were seen in the training data without considering the surrounding region. However, a drawback of training a classifier for each super-pixel is that the histograms associated with each super-pixel are very sparse, often containing only a handful of nonzero-elements. This is due to the nature of the super-pixels: by definition they cover areas that are roughly similar in color and texture. Since the features are fixed-scale and extracted densely, the super-pixels sometimes contain tens or even hundreds of descriptors that quantize to the same visual word.

To overcome the problems caused by the lack of consideration of the surrounding region of each super-pixel and sparse histogram representation, the histograms are applied based on super-pixel neighborhoods. Let G(S, E) be the adjacency graph of super-pixels $s_i$ in an image, and $h_i^0$ be the non-normalized histogram associated with this region. E is the set of edges formed between pairs of adjacent super-pixels $(s_i, s_j)$ in the image and $D(s_i, s_j)$ is the length of shortest path between two super-pixels. Then, $h_i^N$ is the histogram obtained by merging the histograms of the super-pixel $s_i$ and neighbors who are less than N nodes away in the graph:

$$h_i^N = \sum_{s_j | D(s_i, s_j) \leq N} h_j^0 \quad (2)$$

The training framework is unchanged, except that super-pixels are described by the normalized histograms $h_i^N$ in place of $h_i$.

Finally, these 1D merged histogram representations are taken as the input for the binary SVM training module. After the binary classifier is trained, it is applied to classify all super-pixels from all training images. Then, all the super-pixels labeled as wound are gathered by the first stage classifier and an approximately equal number of non-wound super-pixels as the training data set for the next stage of machine learning. For each instance in this set, the dominant color descriptor (DCD) is extracted and train the second stage classifier (which inherently shares the same working scheme with the first stage SVM based classifier) based on these descriptors.

In order to compute this descriptor, the colors present in a given region are first clustered. This results in a small number of colors and the percentages of these colors are calculated. As an option, the variances of the colors assigned to a given dominant color are also computed. The percentages of the colors present in the region should add up to 1. A spatial coherency value is also computed that differentiates between large color blobs versus colors that are spread all over the image. The descriptor is thus defined as following:

$$F = \{(c_i, p_i, v_i), s\}, (i=1, 2, \ldots, N) \quad (3)$$

where $c_i$ is the $i^{th}$ dominant color and $p_i$ is its percentage value and $v_i$ is its color variance. N represents the number of dominant color clusters. The spatial coherency s is a single number that represents the overall spatial homogeneity of the dominant colors in the image. In one instance, the DCD can be easily determined from the early mean shift based super-pixel segmentation results. The reason for the second stage classification is to utilize the color features to further improving the differentiation between skin and wound tissues near the wound boundary.

In the testing process, for an input testing image, same super-pixel segmentation and BoW representation generation will be performed. Then, the first stage binary classifier is applied to identify all "candidate wound" super-pixels. Next, the DCD descriptor is generated for each "candidate wound" super-pixel and input to the second stage binary classifier. Next, a conditional random field (CRF) technique based refinement method is operated to recover more precise boundaries while still maintaining the benefits of histogram merge over the super-pixel neighborhood. Finally, a closing operation, one of the morphology methods, can be performed to eliminate small holes in the detected wound area and further to smooth the wound boundary.

Figure 6:
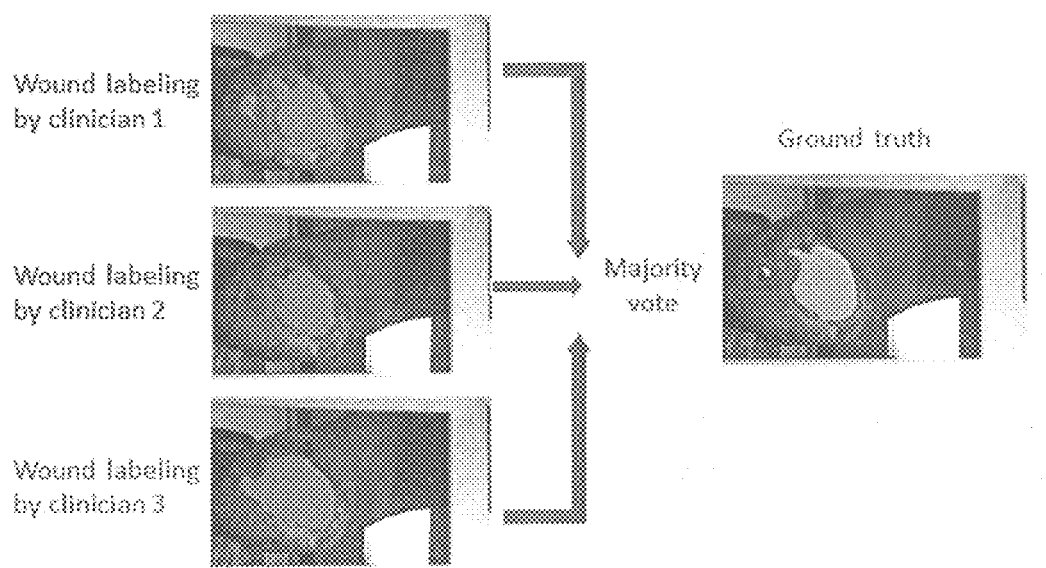
FIG. 6 shows exemplary results of a wound image obtained by a majority vote scheme as used in these teachings.

To train the classifier and also evaluate the wound recognition performance of the method of these teachings, the help of experienced wound clinicians is needed to generate the ground truth wound labels. In one instance, 48 wound images collected from UMass Wound Clinic from 12 patients over 12 months are used. For each image, three clinicians were asked to delineate the wound boundary independently with Photoshop software and a set of electronic drawing pen and panel. Afterwards, the majority vote scheme is used (for each pixel, if 2 or 3 clinicians label it as "wound", then it will be determined as "wound" pixel. Otherwise, it will be determined as "non-wound" pixel). An example of the ground truth generation is illustrated in FIG. 6.

Figure 7:
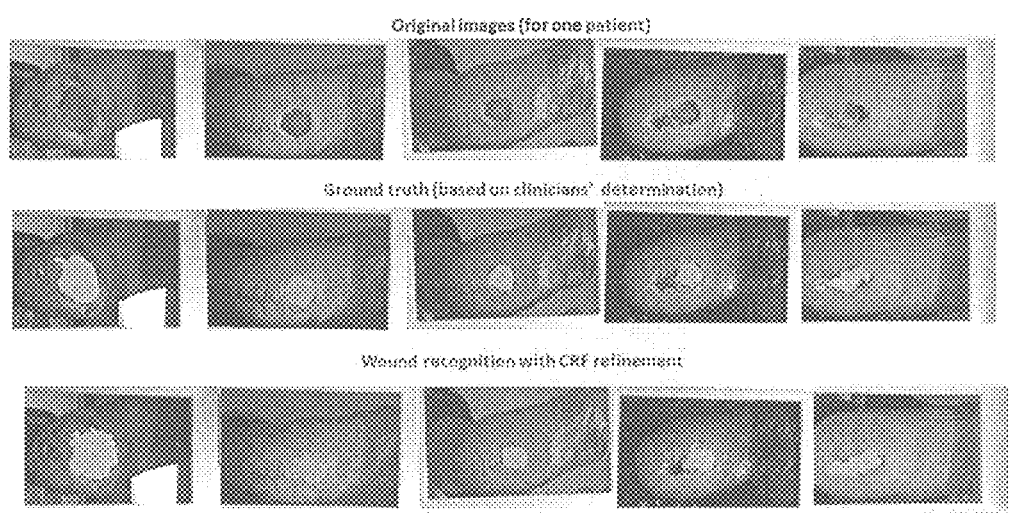
FIG. 7 shows a comparison of original images, images obtained by the majority vote scheme and wound recognition using the machine learning methods of these teachings.

The samples of the wound recognition results on the images of real patients are shown in FIG. 7. It can be seen that this solution provide promising wound boundary determination.

In order to better assess the SVM based wound recognition method, the following testing and evaluation approach is used. First, the leave-one-out cross validation method is adopted to evaluate the model performance on the entire dataset. Specifically, one image is chosen each time from the sample image set as the testing sample and the rest is taken as the training samples used for SVM based model training. Hence, this experiment has to performed for a number of times equal to the size of the entire sample image set (48 times for all 48 wound images) in order to test on the entire image dataset and keep the specified testing image different from all images in the training dataset.

Second, since the wound recognition is a skewed distributed binary class problem, which contains a large number of non-wound super-pixels and a relatively small number of wound super-pixels for each wound image, the accuracy rate cannot be used to evaluate the performance. Instead, the idea of true positive (tp), false positive (fp), false negative (fn) and true negative (tn) respectively defined as in FIG. 8 is used. The matrix shown in this figure is also called the confusion matrix.

Substantial research has been performed on developing a convincing evaluation score based on these four values. The Matthews Correlation Coefficient (MCC) is used in machine learning as a measure of the quality of binary classification. Especially, it takes into account true and false positives and negatives and is generally regarded as a balanced measure which can be used even if the classes are of very different sizes.

The MCC is in essence a correlation coefficient between the observed and predicted binary classification; it returns a value between −1 and +1. A coefficient of +1 represents a perfect prediction, 0 no better than random prediction and −1 indicates total disagreement between prediction and observation. It is defined directly on the confusion matrix as below.

$$MCC = \frac{tp \times tn - fp \times fn}{\sqrt{(tp + fp)(tp + fn)(tn + fp)(tn + fn)}} \quad (4)$$

The experimental results shows that the average MCC value of 48 test images using leave-one-out evaluation method is 0.7, which is 0.1 higher than the commonly regarded standard value of promising object recognition.

In one instance, in the method of these teachings, performing the color segmentation comprises performing a K-mean color clustering algorithm; and evaluating the wound area comprises using a red-yellow-black evaluation model for evaluation of the color segmentation and, in the system of these teachings, the image segmentation component is configured to perform a K-mean color clustering algorithm; and uses a red-yellow-black evaluation model for evaluation of the color segmentation.

Red-Yellow-Black (RYB) Model

After the accurate wound boundary is acquired, the wound area is analyzed within the boundary using some wound description model. Many methods for assessing and classifying open wounds require advanced clinical expertise and experience. Specialized criteria have been developed for diabetic foot ulcers. In order to facilitate the wound management performed by patients themselves at home, there is need for a simple classification system that can be universally applied. The RYB wound classification model which was first proposed in the October 1988 by J. Z. Cuzzell and C. Blanco provide us a consistent, simple model to evaluate the wound (D. Kransner, Wound Care How to Use the Red-Yellow-Black System, the American Journal of Nursing, Vol. 95 (5), 1995, pp. 44-47 which is incorporated by reference herein in its entirety and for all purposes).

The RYB system classifies the wound as red, yellow, black or mixed tissues which represent the different phases of the tissue on the continuum of the wound healing process, respectively. In detail, red tissues are viewed as the inflammatory (reaction) phase, proliferation (regeneration), or maturation (remodeling) phase. On the other hand, yellow tissues stand for the infected or contain slough that aren't ready to heal. At last, black tissues indicate necrotic tissue state, which is not ready to heal either.

Based on the RYB wound evaluation model, the task for wound analysis is equal to clustering all the pixels within the wound boundary into certain color categories. Therefore, all classical clustering method can be applied to solve this task.

K-Mean Algorithm

In data mining, k-means clustering is a method of cluster analysis (see, or example, K means and Hierarchical Clustering, tutorial slides by Andrew W. Moore, 2001, which is incorporated by reference herein in its entirety and for all purposes), which aims to partition n observations into k clusters in which each observation belongs to the cluster with the nearest mean. In one instance, all the pixels within the wound boundary can be viewed as observations. The three colors referred in RYB model are regarded as clusters. The algorithm is graphically illustrated in FIG. 9a.

Figure 9A:
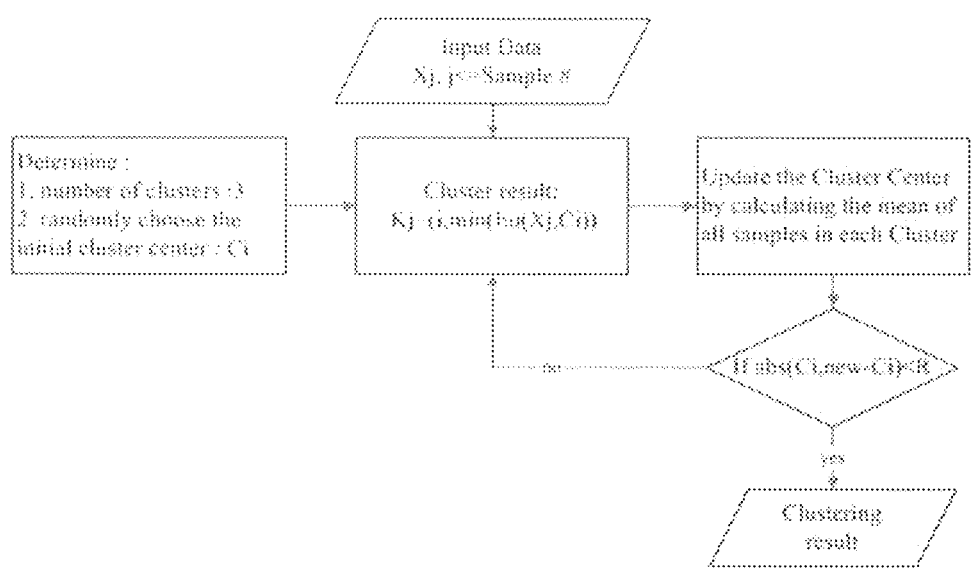
FIG. 9a is a flowchart representation of the K-means algorithm used in these teachings.
Figure 9B:
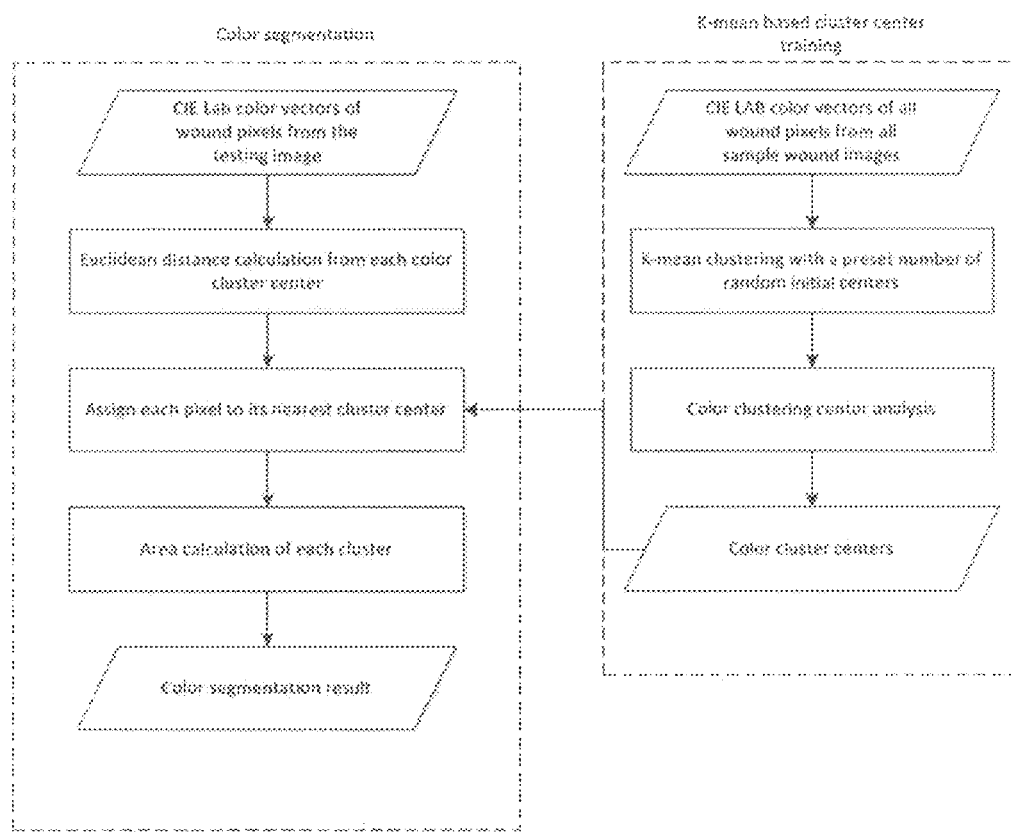
FIG. 9b is a flowchart representation of Color segmentation method of these teachings.
Figure 9C:
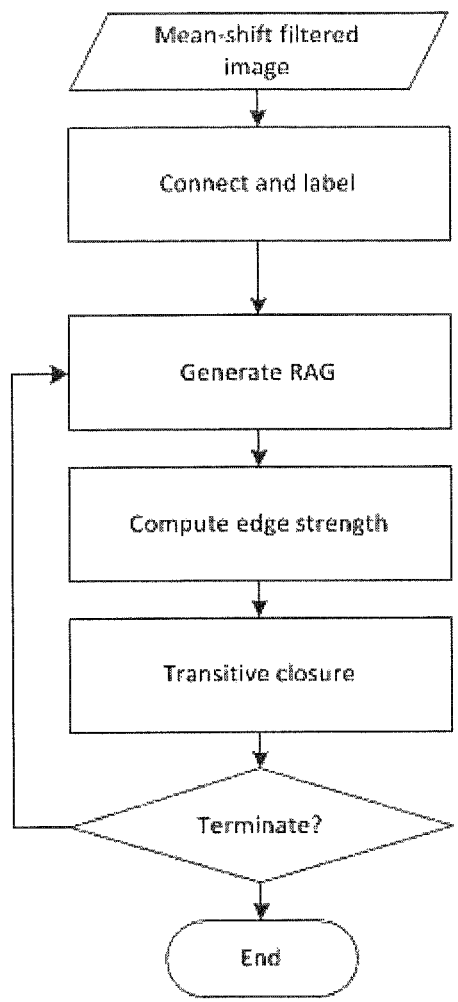
FIG. 9c is a flowchart representation of algorithm flow of the region fusion step of these teachings.
Figure 10A:
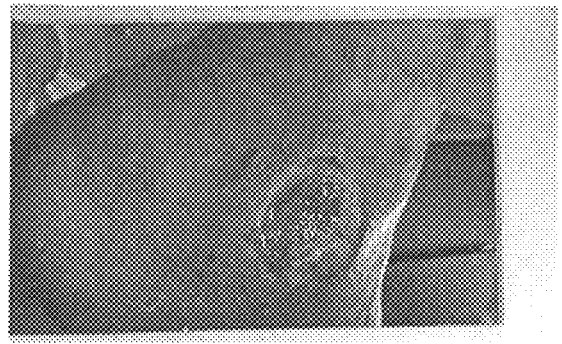
FIGS. 10a-10i show images of wound areas and all results of two color segmentation methods used in these teachings.
Figure 10B:
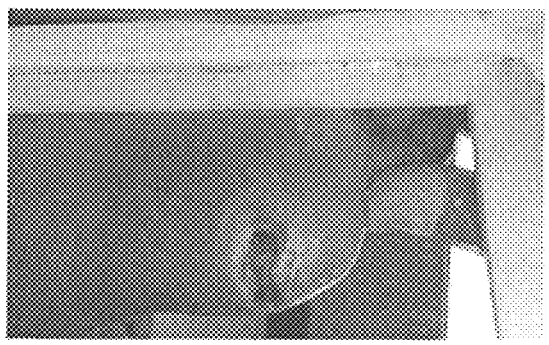
Figure 10C:
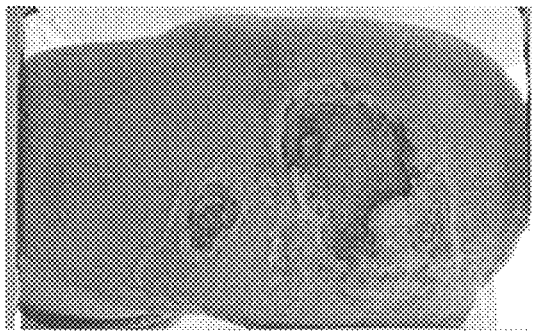
Figure 10D:
Figure 10E:
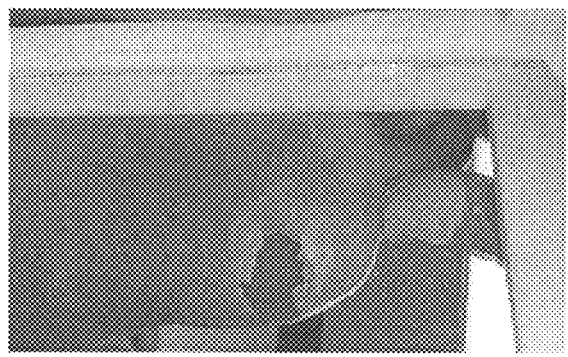
Figure 10F:
Figure 10G:
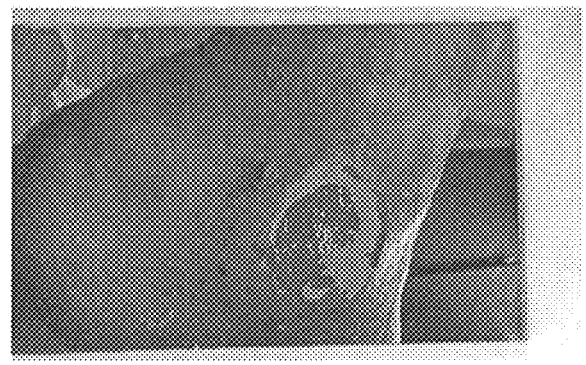
Figure 10H:
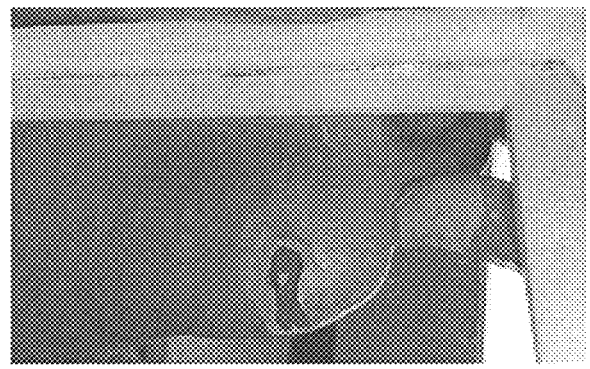
Figure 10I:
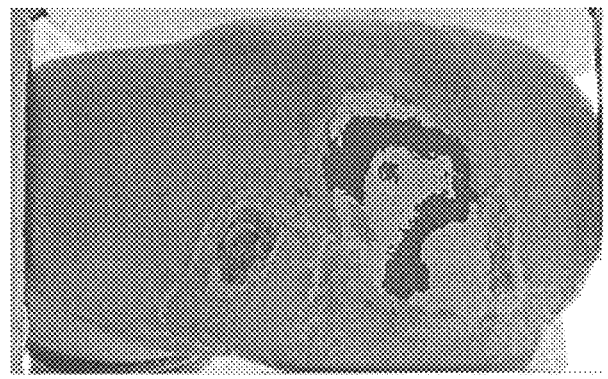

1) The color difference between the cluster center and the target pixel (expressed as Eu in the flowchart in part a) in FIG. 9c is calculated by the standard Euclidean color difference in CIE Lab model.

2) Strictly speaking, K-mean algorithm is a NP-hard problem, which is unable to converge to a solution within limited time when the image size is large enough. However, the iteration can be terminated when the average mean variance of each cluster is smaller than a pre-specified threshold. This heuristic method is expressed as the decision block in part a) of FIG. 9c. In part a) of FIG. 9c, the initial centers are chosen randomly. However, in practice, the initial centers may be specified according to some empirical values such as the Macbeth Color Checker. By this operation, the converging speed will be increased thus making the color clustering process more efficient.

3) As shown in FIG. 9a, the number of cluster is preset to 3. However, the number could be smaller or larger than 3. Some post-processing has to be performed to the resulting clusters. In the present teachings, only the situation that the number of clusters is equal to 3 at most is considered. Therefore, some two or three clusters may have to be combined if they are close to each other enough, which can be equally viewed as the mean value difference of the two or three clusters is smaller than a preset threshold.

In another embodiment, in the method of these teachings, performing the color segmentation includes using a K-mean color clustering algorithm on results of images used on training a classifier and, in the system of these teachings, the image segmentation component is configured to use a K-mean color clustering algorithm on results of images used on training a classifier.

A method similar to Bag-of-Words is used in another embodiment of color segmentation of these teachings. The flow chart of this embodiment is shown in FIG. 9b. There are two major tasks in this algorithm. In the training process, as stated herein above, three experienced wound clinicians were asked to label the wound area using a set of electronic drawing panel, pen and also Photoshop software on the laptop. First, the color vectors are gathered, in CIE Lab color space, for all labeled wound pixels in the sample foot ulcer images. Then, the K-mean clustering algorithm are performed for all color vectors. Instead of using the pre-set standard color center vector, a number of color vector values are randomly selected as the initial centers. It turns out that the setting of the initial centers has no impact on the final color clustering results. The only parameter, which needs to be preset is the cluster number. In one instance, it is set to 10, a relatively large cluster number considering the wound tissues usually only contain 3-5 obviously distinct color types, since this will provide us a more fine classification and also is not too time demanding, which means each pixel is assigned to a cluster center reasonably resembling its own color. After the initial clustering, all the cluster centers are analyzed and several centers with small Euclidean distance in the color space are merged into one. This operation can reduce the final cluster number and form a more representative wound evaluation model. From the ten color cluster centers resulted from the K-mean algorithm, only a number of colors centers (1, 2, 3, 4 in one instance) are quite distinct from each other. Those color centers can be regarded as clusters for yellow, white, black and red, respectively. Some of the other color centers (in one instance from 5-9) can all be classified as one color (red, in one instance) but with different saturation and hues or merged into one of the distinct color centers. The original RYB model is extended to include another cluster center representing the wound tissue in color of white. However, based on clinicians' opinion, the white wound tissue, which is more like the calluses, should not contribute to the final wound healing assessment. Hence, the white tissue is considered as part of the wound area but is not considered when performing the color based wound analysis.

In the segmentation process, the original set of clusters (in number of 10) is used and the assignment is made to each wound pixel in the determined wound area. After that, the pixels assigned to cluster number 5-9 are merged into cluster 4, and the pixels assigned to cluster number 10 are merged into cluster 3, since the Euclidean distance in CIE Lab color space is small enough. The color segmentation results on 5 sample wound images are shown in FIGS. 10a-10i, the original images are displayed in 10a-10c, and the color segmentation results using the K-mean algorithm alone shown in FIGS. 10d-10f. The results from the above described color segmentation algorithm in this report can be seen in FIGS. 10g-10i. After comparison, algorithm combining k-means with the figures selected by the clinicians results in an improvement.

In one instance, in the method of these teachings, evaluating the wound area includes determining a healing score as a method for quantifying a healing status of the wound area and, in the system of these teachings, the wound evaluation component is configured to determine a healing score as a method for quantifying a healing status of the wound area.

Healing Score

One goal of these teachings is to provide more meaningful wound analysis results to the users, including both the clinicians and diabetic patients. For clinicians, the wound area size and different color tissue composition may be sufficient. They can make their diagnosis based on these raw data. However, for ordinary patients assumed to be without any clinical knowledge about wounds, only providing them some absolute numbers does not give them with much help in understanding their actual wound status. Hence, there is a need to translate the raw data into a meaningful numerical value, like a score in the range of 0-100, where larger simply means better. In this report, a numerical wound evaluation value called healing score is used. The basis for calculating the healing score are four indicators: wound area size, red tissue size, yellow tissue size, and black tissue size. As introduced in related references, the red means granulation, which is probably a positive sign for healing. On the other hand, yellow might represent tissues with infection and black stands for necrotic tissues. And these are negative signs for bad healing status. Besides, the shrinking of the entire wound area certainly is a strong positive evidence of good healing status. Note that since there is no official described clinical correspondence for the white tissue, only the red, yellow and black tissues are considered for the calculation of the healing score and will merge the white cluster to the closet one of the three types.

Considering all of the factors above, a healing score calculation formula is provided herein below. The Healing Score formulation has three components:

1) A Healing Score based on wound area, which will have an initial score of 50, given that the wound area can become larger or smaller 2) A Healing Score based on the color with the wound boundary. Here, the initial score is not fixed, but will be bounded by the range 0-100, such that all red will produce a Healing Score of 100, all black will produce a Healing Score 0, and some combination of red, white, yellow and black will generate a Healing Score 0<score<100.

3) A composite Healing Score, which will be a weighted average of the Healing Score based on wound area and the Healing Score based on the color with the wound boundary. The weight may be constant or may be influenced by the size of the wound area.

Healing Score Based on Wound Area

As stated, the initial value is defined to be 50. Let $\alpha_n$ be the wound area in week n and $S_n^A$ be the wound area score in week n. $a_0$ is the initial wound area size acquired when the patient use the system for the first time. Thus, $S_n^A = f(a_0, a_n)$ and $S_0^A = f(a_0, a_0) = 50$, where f is supposed to be function taking $a_n$ and $a_0$ as its parameters.

$$S_n^A = \left(1 - \frac{a_n - a_0}{a_0}\right)50, \; a_n \leq 2a_0 \quad (5)$$

$$S_n^A = 0, \; a_n > 2a_0$$

As $a_n$ varies from 0 to $2a_0$, $S_n^A$ decreases linearly from 100 to 0. For values of an $a_n > 2a_0$, $S_n^A = 0$. This should be reasonable assumption that once the wound become twice as large as the initial size there is no sign of healing at all. The wound area healing score is a relative numerical value which takes the initial wound area size as the reference.

Healing Score Based on Color with the Wound Boundary

Let $S_n^T$ be the Healing Score based on the color with the wound boundary in week n. Similar to $a_n$, the ratio of red area, yellow area and black area are defined, within the wound boundary, as $r_n$, $y_n$ and $b_n$, respectively, and where subscript 'n' refers to week n. Clearly, $r_n + y_n + b_n = 1$ in general, and specifically $r_0 + y_0 + b_0 = 1$.

Based on wound evaluation theory, $S_n^T$ must be formulated so that $S_n^T = 100$ for $r_n = 1$; $y_n = b_n = 0$, and $S_n^T = 0$ for $b_n = 1$; $r_n = y_n = 0$. The following formulation for $S_n^T$ is proposed:

$$S_n^T = \frac{1 + r_n - 0.5y_n - b_n}{2} 100 \quad (6)$$

It is easily verified that $S_n^T(r_n = 1; y_n = b_n = 0) = 100$ and that $S_n^T(b_n = 1; y_n = r_n = 0) = 0$. Consider also the case where $r_n = y_n = b_n = 0333$, giving $S_n^T = 41.7$.

Composite Healing Score

Let $S_n$ be the overall, or composite, Healing Score:

$$S_n = w_A S_n^A + w_T S_n^T \quad (7)$$

where $w_A$ and $w_T$ are weights, such that $w_A + w_T = 1$. This allows us to formulate $S_n$ as $$S_n = w_A S_n^A + (1 - w_A) S_n^T \quad (8)$$

A simple (and acceptable) solution is to set $w_A = 0.5$. $w_A$ does not have be a constant; instead, $w_A$ should have a greater influence when the wound is close to being healed and hence the area is small. Specifically, in one instance, $w_A$ increases linear from $w_A = 0.5$ to $w_A = 1.0$, as $S_n^A$ increases linearly from 0 to 100. In other words, $$w_A = 0.5 + \frac{0.5}{100} S_n^A, \text{ giving} \quad (9)$$

$$S_n = [0.5 + 0.05 S_n^A] S_n^A + [0.5 - 0.005 S_n^A] S_n^T$$

An example of applying the proposed healing score to evaluate the wound status is based on five images. The wound analysis data for these five images are shown in Table 1. After calculation, the healing score for these four wound images are 82.78, 87.86, 84.75, and 75.59 (the first image is viewed as the base reference and not scored). From Image 1 to 2, the wound area is shrinking. From Image 2 to 3, only a small size decrease of the wound area is observed. Hence, there is also a tiny increase of the healing score by 4.4 points. From part Image 3 to 4, more surgical sutures were exposed and more yellow tissues occurred. On the other hand, the size of the entire wound area didn't change too much. Corresponding to this trend, the healing score is nearly 3 points lower than the previous time. Finally, from part Image 4 to 5, there are extra yellow tissues generated on the outer part of the wound and the red tissues are shrinking. On the other hand, the wound and black tissue area are decreased in a tiny degree. Hence, the healing score decreased by nearly 9 points.

TABLE 1

Wound assessment results (area unit: mm²)

|  | Image 1 | Image 2 | Image 3 | Image 4 | Image 5 |
| --- | --- | --- | --- | --- | --- |
| Healing score |  | 82.78 | 87.86 | 84.75 | 75.59 |
| Wound area | 1126.57 | 403.09 | 293.17 | 279.34 | 457.39 |
| Red area | 791.21 | 353.25 | 282.84 | 214.95 | 106.46 |
| Yellow area | 246.42 | 39.22 | 10.33 | 43.41 | 324.31 |
| Black area | 88.94 | 10.62 | 0 | 20.98 | 26.62 |

Image Capture Box

In one embodiment, the system of these teachings includes an imaging component having a first front surface mirror and a second front surface mirror, the second front surface mirror being disposed at a right angle to the first front surface mirror, the imaging component being configured such that the body part is positioned above the first and second front surface mirrors and away from an axis bisecting the right angle; and wherein the image acquisition device is positioned above the first and second front surface mirrors, away from the axis bisecting the right angle and on an opposite side of the axis bisecting the right angle from the body part.

Figure 11:
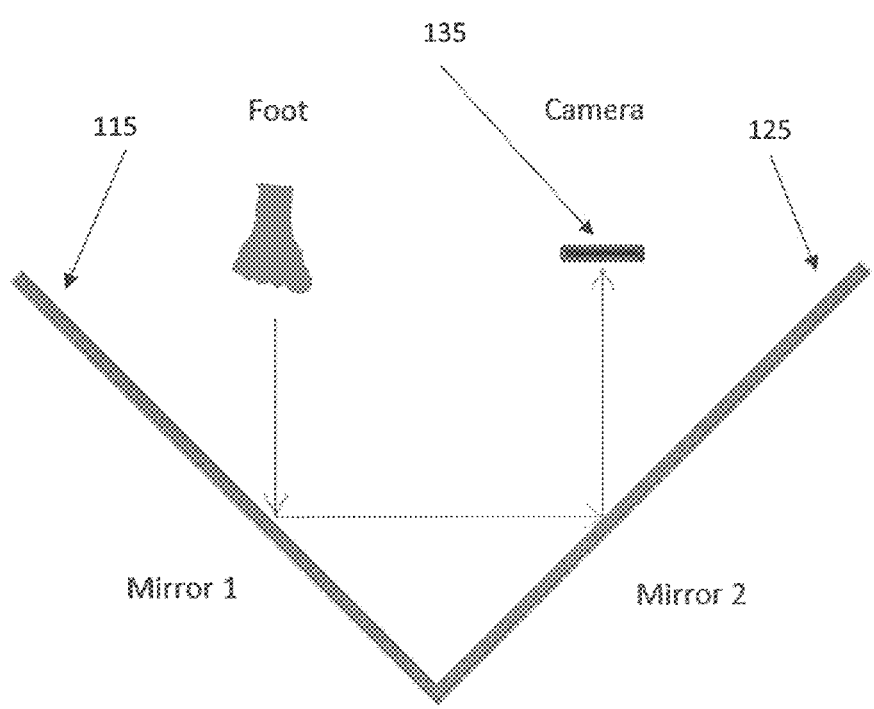
FIG. 11 is a schematic representation of a component of one embodiment of the system of these teachings.

To ensure consistent image capture conditions and also to facilitate a convenient image capture process for patients with type 2 diabetes, an image capture device was designed in the shape of a box. This device is referred to as "the Image Capture Box". The image capture box was designed as a compact, rugged and inexpensive device that: (i) allows patients to both view the sole of their foot on the screen of a device having an image capture components (for example, a handheld portable communication device such as, but not limited to, a smartphone) and to capture an image since the majority of patients' wounds occur on the soles of their feet, (ii) allows patients to rest their feet comfortably, without requiring angling of the foot or the image capture component 135 (in one instance, a smartphone camera), as patients may be overweight and have reduced mobility, and (iii) accommodates image viewing and capture of left foot sole as well as right foot sole. To achieve these objectives, two front surface mirrors 115, 125 are used, placed at an angle of 90° with respect to each other, and with the common line of contact tilted 45° with respect to horizontal. A schematic drawing of basic optical principle for foot imaging is shown in FIG. 11. The optical path is represented by straight lines with arrows indicating the direction.

Figure 12C:
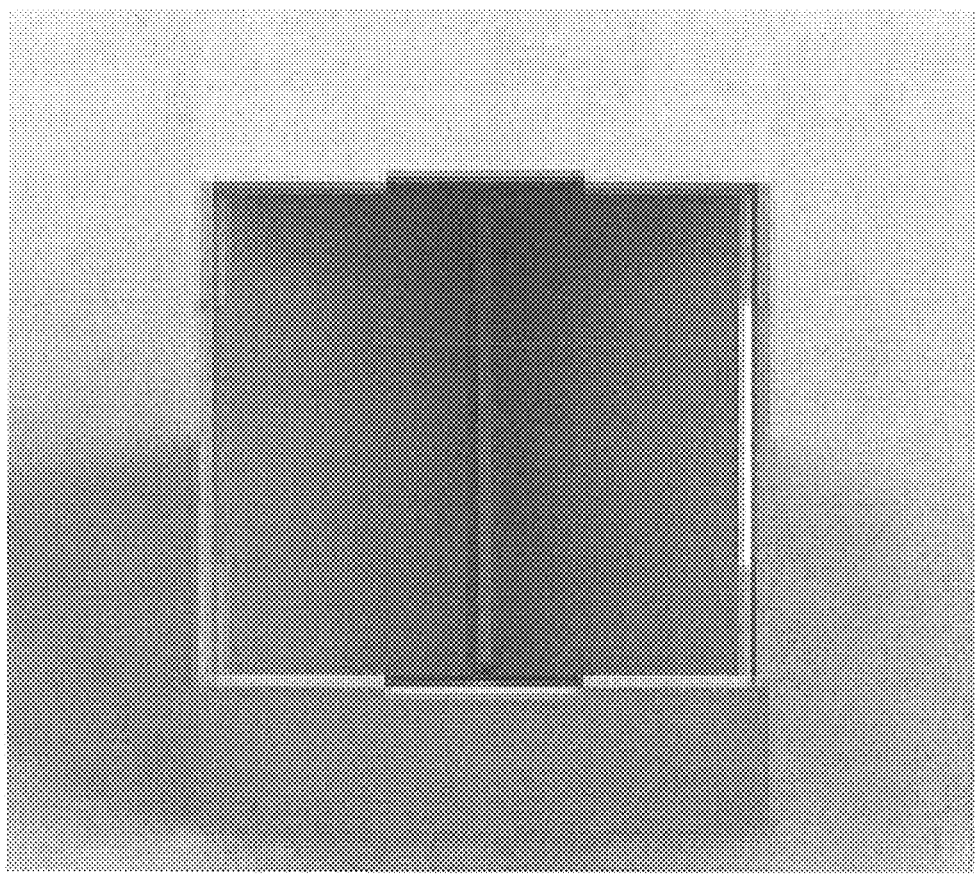

A SolidWorks™ 3D rendering of the image capture box is shown in FIGS. 12a-12c. As seen in this figure, the entire box has a rectangular trapezoid shape. Rectangular openings for placing the foot and smartphone are cut into the slanted surface, shown in FIG. 12b, which is at 45° with respect to horizontal. In this case, the patient can rest his/her foot comfortably and view his/her wound on the LCD display of the smartphone camera. When using the box, the patient needs to ensure that the wound is completely located within the opening by simply observing the image displayed on the smartphone.

Figure 13:
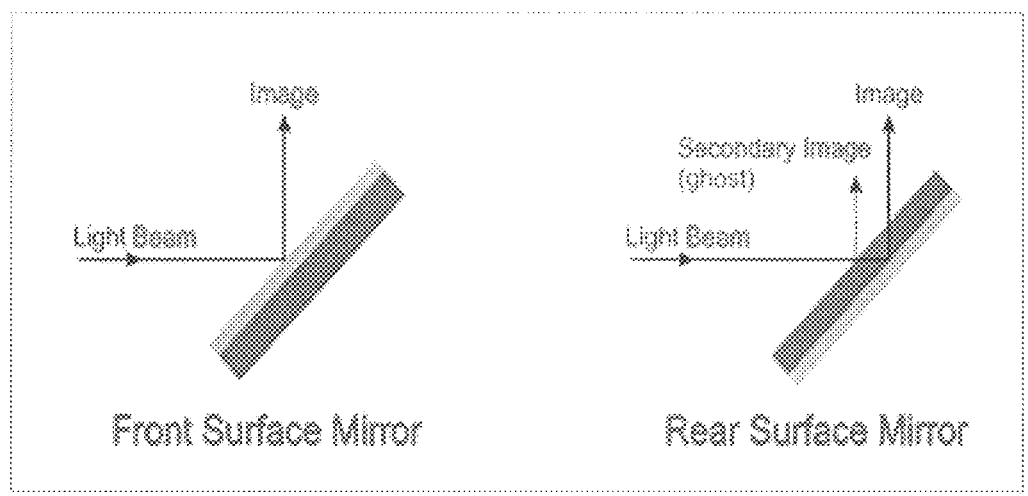
FIG. 13 is a schematic representation of front surface mirrors as used in one component of the system of these teachings.
Figure 13:
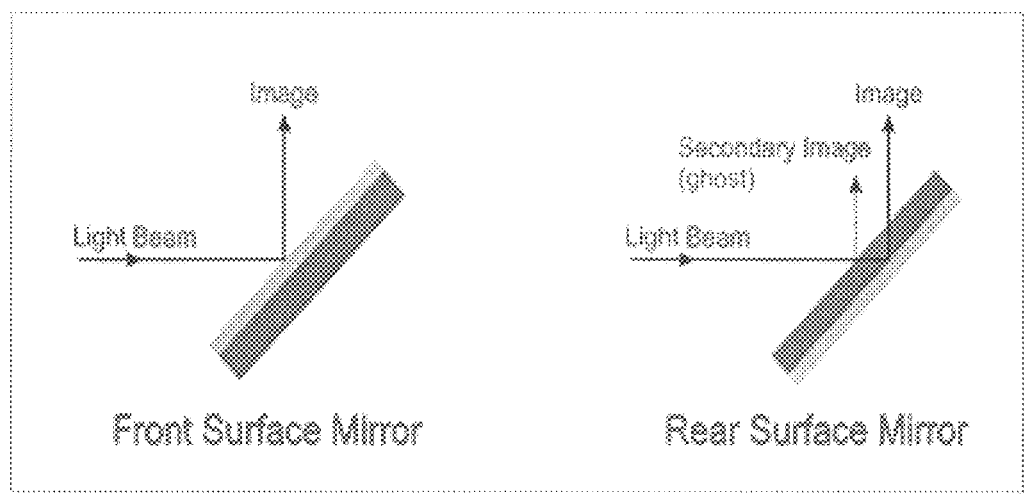

To avoid the ghost image effect associated with normal back surface mirrors (reflective surface on the back side of the glass), front surface mirrors (reflective surface on the front side) are needed, as illustrated in FIG. 12a. The optical paths for both the front surface mirror and the normal mirror are shown in FIG. 13.

In one embodiment, the image acquisition device, the image analysis component, the image segmentation component and the wound evaluation component of the system of these teachings are comprised in a handheld portable electronic device. In that embodiment, the handheld portable electronic/communication device includes the image acquisition device, the image acquisition device being configured for capturing an image of a body part including a wound area, one or more processors, and computer usable media having computer readable code embodied therein that, when executed by the one or more processors, causes the one or more processors to extract a boundary of the wound area, perform color segmentation within the boundary of the wound area, wherein the wound area is divided into a plurality of segments, each segment being associated with a color indicating a healing condition of the segment and evaluate the wound area.

Descriptions of exemplary implementations of a mobile-based system can be found in, for example, U.S. Publication No. 2012/0190947 to Chon et al., which is incorporated herein by reference in its entirety for all purposes.

Figure 14:
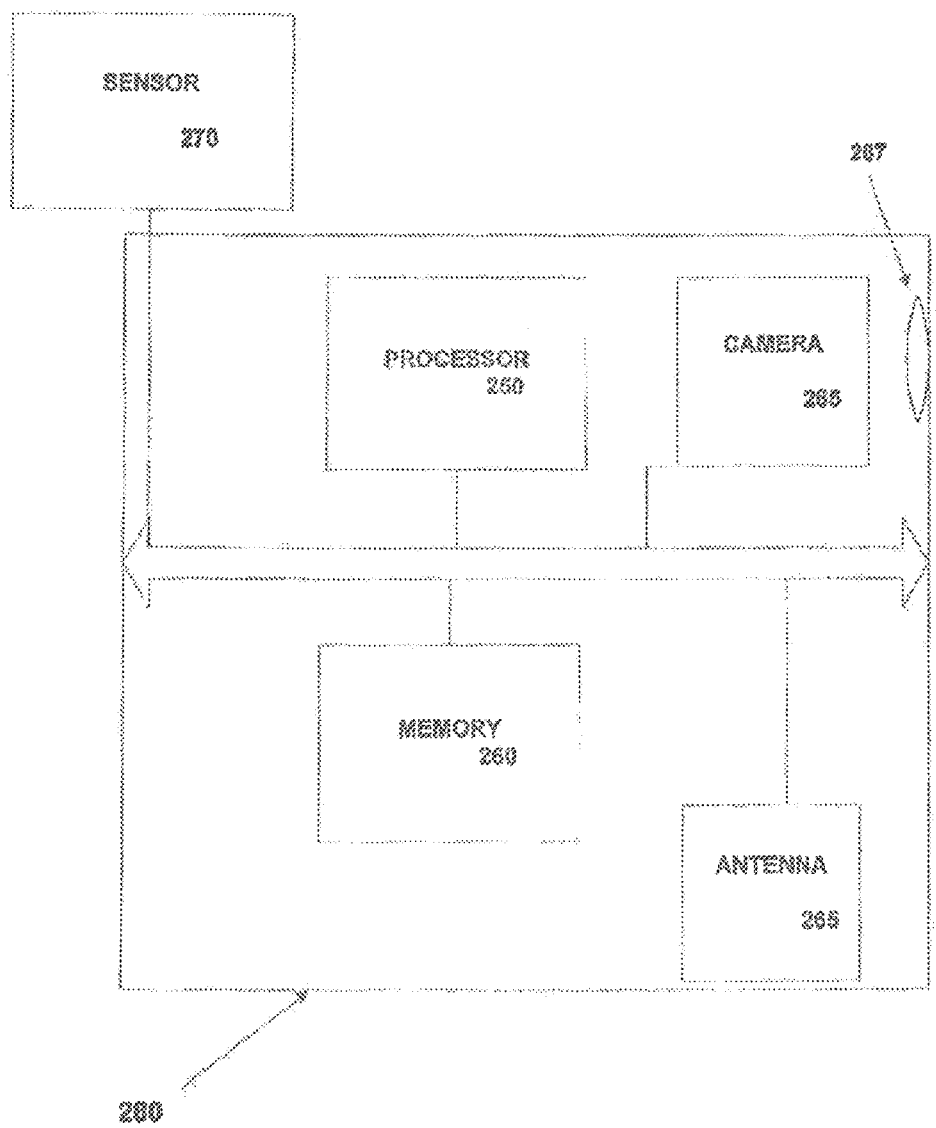
FIG. 14 is a schematic block diagram representation of another embodiment of the system of these teachings.

FIG. 14 is a block diagram representation of one embodiment of the system of these teachings. Referring to FIG. 14, in the embodiment shown therein, a mobile communication system 280 includes a processor 250 and one or more memories 260. In the embodiment shown in FIG. 14, a camera 265, where the camera as an objective lens 267, can also supply the physiological indicators signal to the mobile communication device 280. The one or more memories 260 have computer usable code embodied therein that causes the processor 250 to that causes the processor to extract a boundary of the wound area, perform color segmentation within the boundary of the wound area, wherein the wound area is divided into a plurality of segments, each segment being associated with a color indicating a healing condition of the segment and evaluate the wound area. In one or more instances, the computer readable code causes the processor 250 to perform the implement the methods described hereinabove.

The one or more memories 260 represent one embodiment of computer usable media having computer readable code embodied therein that causes a processor to implement the methods of these teachings. Embodiments of the method of these teachings are described hereinabove and the computer readable code can cause a processor to implement those embodiments.

In the embodiment shown in FIG. 14, the mobile communication device 280 also includes an antenna 265 that enables communications through one or more of a variety of wireless protocols or over wireless networks.

In another embodiment, in the system of these teachings, the image acquisition device is comprised in a handheld portable electronic device; and the image analysis component, and the wound evaluation component are comprised in a computing component. The handheld portable electronic device, such as that shown in FIG. 14, includes the image acquisition device, the image acquisition device being configured for capturing an image of a body part including a wound area, one or more processors, and computer usable media having computer readable code embodied therein that, when executed by the one or more processors, causes the one or more processors to transmit the image to the computing component.

Figure 15:
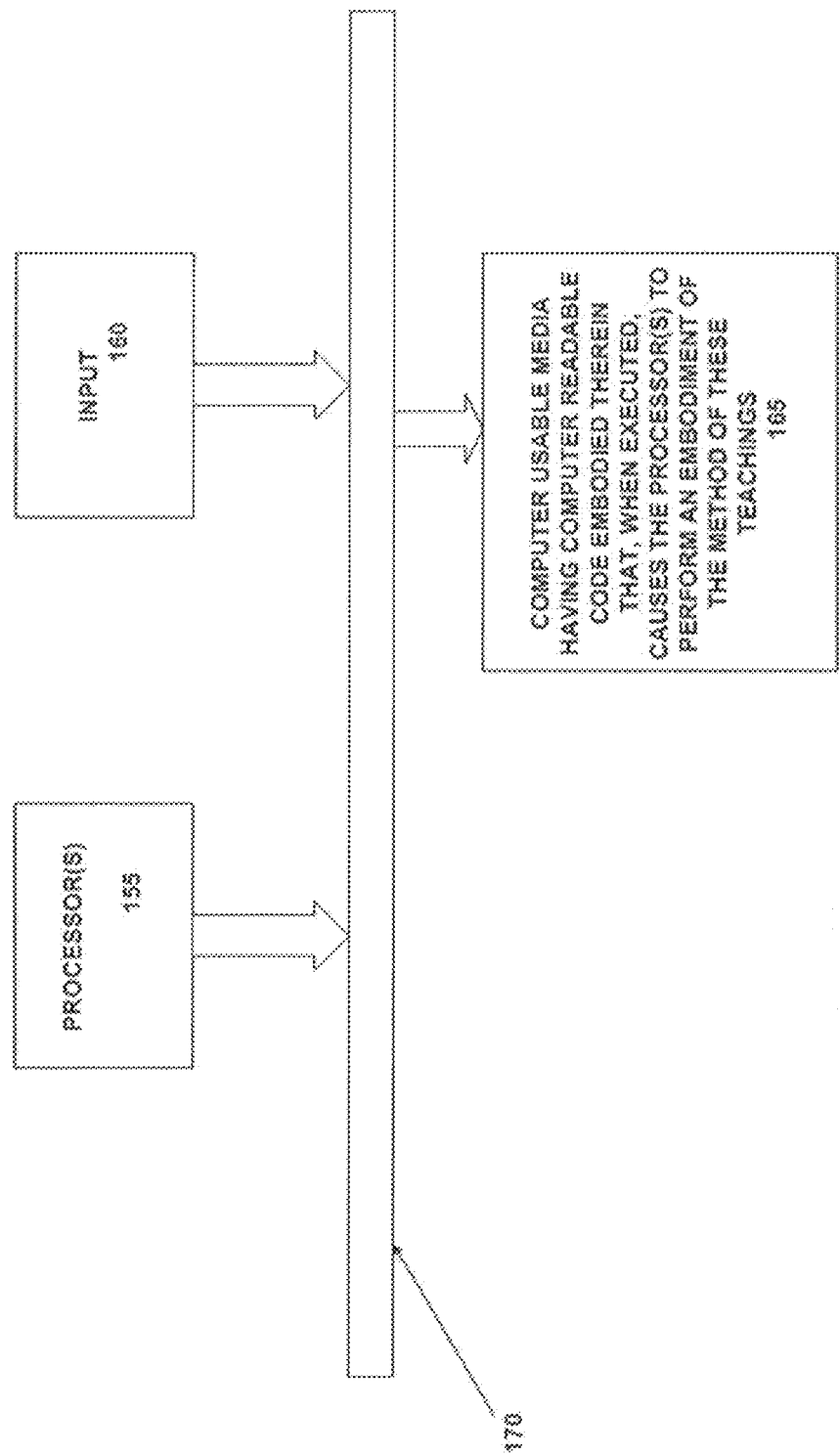
FIG. 15 is a schematic block diagram presentation of another component of a further embodiment of the system of these teachings.

The computing component could have a structure such as that shown in FIG. 15. Referring to FIG. 15, in the structure shown there in, one or more processors 155 are operatively connected to an input component 160, which could receive the images transmitted by the handheld portable electronic/communication device, and to computer usable media 165 that has computer readable code embodied therein, which, when executed by the one or more processors 155, causes the one or more processors 155 to perform the method of these teachings. The one or more processors 155, the input component 160 and the computer usable media 165 are operatively connected by means of a connection component 170.

In one instance, the computer readable code embodied in the computer usable media 165 of the computing component causes the one or more processors 155 to receive the image from the handheld portable electronic device, extract a boundary of the wound area, perform color segmentation within the boundary of the wound area, wherein the wound area is divided into a plurality of segments, each segment being associated with a color indicating a healing condition of the segment and evaluate the wound area.

Figure 16:
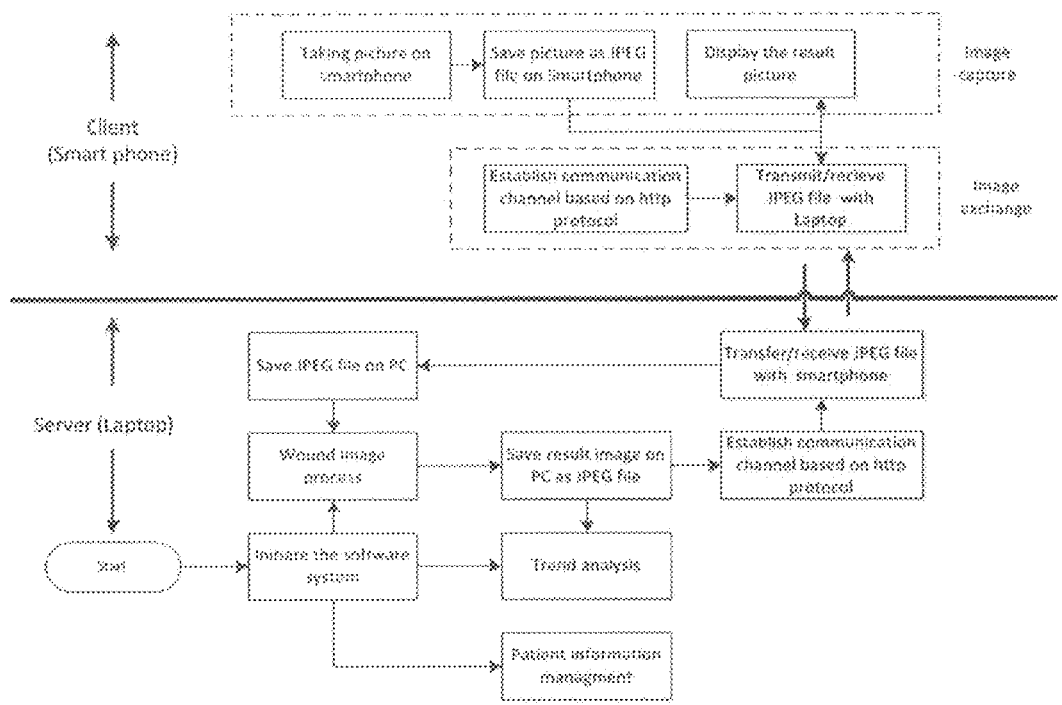
FIG. 16 is a flowchart representation of the use of a further embodiment of the system of these teachings.

An exemplary embodiment of the system including a handheld portable electronic/communication device and a computing component (also referred to as a collaborative or cooperative system, is shown in FIG. 16. Referring to FIG. 16, in the exemplary embodiment shown therein, the handheld portable electronic/communication device is a smart phone and the computing device is a laptop. The smartphone will play the role of client in the communication scheme. It will accomplish the following task sequentially: 1) take the picture of the wound and save on the specified directory on the SD card; 2) make request to the server and send the JPEG file of wound image to the laptop by function "post( )" in an http library and 3) receive the analyzed image file sent by laptop and display it on the screen. The laptop will be viewed as the server party, which will 1) listen to the request of the client and get the image file sent by the client by "dopost( )" function, 2) accomplish the wound image process to he received wound image and 3) send the JPEG file of the processed image back to the smartphone (client) as a response.

The following is a disclosure by way of example of a device configured to execute functions (hereinafter referred to as computing device) which may be used with the presently disclosed subject matter. The description of the various components of a computing device is not intended to represent any particular architecture or manner of interconnecting the components. Other systems that have fewer or more components may also be used with the disclosed subject matter. A communication device may constitute a form of a computing device and may at least include a computing device. The computing device may include an inter-connect (e.g., bus and system core logic), which can interconnect such components of a computing device to a data processing device, such as a processor(s) or microprocessor(s), or other form of partly or completely programmable or pre-programmed device, e.g., hard wired and or application specific integrated circuit ("ASIC") customized logic circuitry, such as a controller or microcontroller, a digital signal processor, or any other form of device that can fetch instructions, operate on pre-loaded/pre-programmed instructions, and/or followed instructions found in hard-wired or customized circuitry to carry out logic operations that, together, perform steps of and whole processes and functionalities as described in the present disclosure.

In this description, various functions, functionalities and/or operations may be described as being performed by or caused by software program code to simplify description. However, those skilled in the art will recognize what is meant by such expressions is that the functions result from execution of the program code/instructions by a computing device as described above, e.g., including a processor, such as a microprocessor, microcontroller, logic circuit or the like. Alternatively, or in combination, the functions and operations can be implemented using special purpose circuitry, with or without software instructions, such as using Application-Specific Integrated Circuit (ASIC) or Field-Programmable Gate Array (FPGA), which may be programmable, partly programmable or hard wired. The application specific integrated circuit ("ASIC") logic may be such as gate arrays or standard cells, or the like, implementing customized logic by metallization(s) interconnects of the base gate array ASIC architecture or selecting and providing metallization(s) interconnects between standard cell functional blocks included in a manufacturer's library of functional blocks, etc. Embodiments can thus be implemented using hardwired circuitry without program software code/instructions, or in combination with circuitry using programmed software code/instructions.

Thus, the techniques are limited neither to any specific combination of hardware circuitry and software, nor to any particular tangible source for the instructions executed by the data processor(s) within the computing device. While sonic embodiments can be implemented in fully functioning computers and computer systems, various embodiments are capable of being distributed as a computing device including, e.g., a variety of forms and capable of being applied regardless of the particular type of machine or tangible computer-readable media used to actually effect the performance of the functions and operations and/or the distribution of the performance of the functions, functionalities and/or operations.

The interconnect may connect the data processing device to define logic circuitry including memory. The interconnect may be internal to the data processing device, such as coupling a microprocessor to on-board cache memory or external (to the microprocessor) memory such as main memory, or a disk drive or external to the computing device, such as a remote memory, a disc farm or other mass storage device, etc. Commercially available microprocessors, one or more of which could be a computing device or part of a computing device, include a PA-RISC series microprocessor from Hewlett-Packard Company, an 80×86 or Pentium series microprocessor from Intel Corporation, a PowerPC microprocessor from IBM, a Sparc microprocessor from Sun Microsystems, Inc, or a 68xxx series microprocessor from Motorola Corporation as examples.

The inter-connect in addition to interconnecting such as microprocessor(s) and memory may also interconnect such elements to a display controller and display device, and/or to other peripheral devices such as input/output (I/O) devices, e.g., through an input/output controller(s). Typical I/O devices can include a mouse, a keyboard(s), a modem(s), a network interface(s), printers, scanners, video cameras and other devices which are well known in the art. The interconnect may include one or more buses connected to one another through various bridges, controllers and/or adapters. In one embodiment the I/O controller includes a USB (Universal Serial Bus) adapter for controlling USB peripherals, and/or an IEEE-1394 bus adapter for controlling IEEE-1394 peripherals.

The memory may include any tangible computer-readable media, which may include but are not limited to recordable and non-recordable type media such as volatile and non-volatile memory devices, such as volatile RAM (Random Access Memory), typically implemented as dynamic RAM (DRAM) which requires power continually in order to refresh or maintain the data in the memory, and non-volatile ROM (Read Only Memory), and other types of non-volatile memory, such as a hard drive, flash memory, detachable memory stick, etc. Non-volatile memory typically may include a magnetic hard drive, a magnetic optical drive, or an optical drive (e.g., a DVD RAM, a CD ROM, a DVD or a CD), or other type of memory system which maintains data even after power is removed from the system.

A server could be made up of one or more computing devices. Servers can be utilized, e.g., in a network to host a network database, compute necessary variables and information from information in the database(s), store and recover information from the database(s), track information and variables, provide interfaces for uploading and downloading information and variables, and/or sort or otherwise manipulate information and data from the database(s). In one embodiment a server can be used in conjunction with other computing devices positioned locally or remotely to perform certain calculations and other functions as may be mentioned in the present application.

At least some aspects of the disclosed subject matter can be embodied, at least in part, utilizing programmed software code/instructions. That is, the functions, functionalities and/or operations techniques may be carried out in a computing device or other data processing system in response to its processor, such as a microprocessor, executing sequences of instructions contained in a memory, such as ROM, volatile RAM, non-volatile memory, cache or a remote storage device. In general, the routines executed to implement the embodiments of the disclosed subject matter may be implemented as part of an operating system or a specific application, component, program, object, module or sequence of instructions usually referred to as "computer programs," or "software." The computer programs typically comprise instructions stored at various times in various tangible memory and storage devices in a computing device, such as in cache memory, main memory, internal or external disk drives, and other remote storage devices, such as a disc farm, and when read and executed by a processor(s) in the computing device, cause the computing device to perform a method(s), e.g., process and operation steps to execute an element(s) as part of some aspect(s) of the method(s) of the disclosed subject matter.

A tangible machine readable medium can be used to store software and data that, when executed by a computing device, causes the computing device to perform a method(s) as may be recited in one or more accompanying claims defining the disclosed subject matter. The tangible machine readable medium may include storage of the executable software program code/instructions and data in various tangible locations, including for example ROM, volatile RAM, non-volatile memory and/or cache. Portions of this program software code/instructions and/or data may be stored in any one of these storage devices. Further, the program software code/instructions can be obtained from remote storage, including, e.g., through centralized servers or peer to peer networks and the like. Different portions of the software program code/instructions and data can be obtained at different times and in different communication sessions or in a same communication session. The software program code/instructions and data can be obtained in their entirety prior to the execution of a respective software application by the computing device. Alternatively, portions of the software program code/instructions and data can be obtained dynamically, e.g., just in time, when needed for execution. Alternatively, some combination of these ways of obtaining the software program code/instructions and data may occur, e.g., for different applications, components, programs, objects, modules, routines or other sequences of instructions or organization of sequences of instructions, by way of example. Thus, it is not required that the data and instructions be on a single machine readable medium in entirety at any particular instance of time.

In general, a tangible machine readable medium includes any tangible mechanism that provides (i.e., stores) information in a from accessible by a machine (i.e., a computing device, which may be included, e.g., in a communication device, a network device, a personal digital assistant, a mobile communication device, whether or not able to download and run applications from the communication network, such as the Internet, e.g., an I-phone, Blackberry, Droid or the like, a manufacturing tool, or any other device including a computing device, comprising one or more data processors, etc.

For the purposes of describing and defining the present teachings, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Although these teachings have been described with respect to various embodiments, it should be realized these teachings are also capable of a wide variety of further and other embodiments within the spirit and scope of the appended claims.

The invention claimed is:

1. A system for assessing wound, comprising:
an image acquisition device configured for capturing an image of a body part including a wound area;
a segmentation component configured to segment the image into a number of regions;
a region merging component configured to merge regions from the number of regions in order to obtain a smaller number of regions and compensate for over segmentation;
a wound boundary determination component configured for extracting a boundary of the wound area;
an image color segmentation component configured for performing color segmentation within the boundary of the wound area, wherein the wound area is divided into a plurality of segments, each segment being associated with a color indicating a healing condition of the segment, and
a wound evaluation component configured for evaluating the wound area; wherein the wound evaluation component is configured to determine a quantitative healing score as a method for quantifying a healing status of the wound area; the quantitative healing score being based on the wound area and color in the wound boundary; wherein the quantitative healing score is a wound evaluation value;
the quantitative healing score comprising a first component determined from a wound area at a predetermined time and an initial wound area and a second component determined from a ratio of areas of each color from red, yellow and black;
wherein the quantitative healing score comprises a sum of a product of a first predetermined weight times the first component and a product of a second predetermined weight times the second component;
wherein the system is used for assessing chronic wounds and ulcers including chronic foot wounds and ulcers from type 2 diabetes.

2. The system of claim 1, wherein the segmentation component is configured to perform mean shift segmentation.

3. The system of claim 1, wherein the wound boundary determination component is configured to use a trained classifier.

4. The system of claim 1, wherein the image color segmentation component is configured to perform a K-mean color clustering algorithm; and uses a red-yellow-black evaluation model for evaluation of the color segmentation.

5. The system of claim 1, wherein the image acquisition device, the segmentation component, the region merging component, the wound boundary determination component, the image color segmentation component and the wound evaluation component are comprised in a handheld portable electronic device; and wherein the handheld portable electronic device comprises: the image acquisition device; the image acquisition device being configured for capturing an image of a body part including a wound area; one or more processors; and non-transitory computer usable media having computer readable code that, when executed by the one or more processors, causes the one or more processors to: segment the image into a number of regions; merge regions from the number of regions in order to obtain a smaller number of regions and compensate for over segmentation; extract a boundary of the wound area; perform color segmentation within the boundary of the wound area, wherein the wound area is divided into a plurality of segments, each segment being associated with a color indicating a healing condition of the segment; and evaluate the wound area; wherein evaluating the wound area comprises determining a quantitative healing score as a method for quantifying a healing status of the wound area; the quantitative healing score being dependent on the wound area and on color in the wound boundary.

6. The system of claim 1, wherein the image acquisition device is comprised in a handheld portable electronic device; and wherein the segmentation component, the region merging component, the wound boundary determination component, and the wound evaluation component are comprised in a computing component; and wherein the handheld portable electronic device comprises: the image acquisition device; the image acquisition device being configured for capturing an image of a body part including a wound area; one or more first processors; and non-transitory first computer usable media having computer readable code that, when executed by the one or more first processors, causes the one or more processors to: transmit the image to the computing component; and wherein the computing component comprises: one or more second processors; and non-transitory second computer usable media having computer readable code that, when executed by the one or more processors, causes the one or more second processors to: receive the image from the handheld portable electronic device; segment the image into a number of regions; merge regions from the number of regions in order to obtain a smaller number of regions and compensate for over segmentation; extract a boundary of the wound area; perform color segmentation within the boundary of the wound area, wherein the wound area is divided into a plurality of segments, each segment being associated with a color indicating a healing condition of the segment; and evaluate the wound area; wherein evaluating the wound area comprises determining the quantitative healing score as a method for quantifying a healing status of the wound area; the quantitative healing score being based on the wound area and color in the wound boundary.

7. The system of claim 1, wherein the segmentation component, the region merging component, the wound boundary determination component, and the wound evaluation component are comprised in a computing component; and wherein the computing component comprises: one or more second processors; and non-transitory second computer usable media having computer readable code that, when executed by the one or more processors, causes the one or more second processors to: receive the image from the image acquisition device; segment the image into a number of regions; merge regions from the number of regions in order to obtain a smaller number of regions and compensate for over segmentation; extract a boundary of the wound area; perform color segmentation within the boundary of the wound area, wherein the wound area is divided into a plurality of segments, each segment being associated with a color indicating a healing condition of the segment; and evaluate the wound area; wherein evaluating the wound area comprises determining the quantitative healing score as a method for quantifying a healing status of the wound area; the quantitative healing score being based on the wound area and color in the wound boundary.

8. The system of claim 1 further comprising: an imaging component comprising: a first front surface mirror; and a second front surface mirror; the second front surface mirror being disposed at a right angle to the first front surface mirror; wherein the imaging component is configured such that an optical path originating at the body part is reflected at one of the first front surface mirror and the second front surface mirror, subsequently reflected at another one of the first front surface mirror and the second front surface mirror and terminates at the image acquisition device; wherein the body part is positioned above the first and second front surface mirrors and away from an axis bisecting the right angle; and wherein the image acquisition device is positioned above the first and second front surface mirrors, away from the axis bisecting the right angle and on an opposite side of the axis bisecting the right angle from the body part.

* * * * *